United States Patent
Lin et al.

(10) Patent No.: US 9,636,323 B2
(45) Date of Patent: May 2, 2017

(54) METHOD OF TREATING CANCER THAT OVEREXPRESSES TOPBP1

(71) Applicants: Weei-Chin Lin, Bellaire, TX (US); Pinki Chowdhury, Farmington Hills, MI (US); Gregory E. Lin, Bellaire, TX (US); Kang Liu, Pearland, TX (US); Yongcheng Song, Pearland, TX (US); Fang-Tsyr Lin, Bellaire, TX (US)

(72) Inventors: Weei-Chin Lin, Bellaire, TX (US); Pinki Chowdhury, Farmington Hills, MI (US); Gregory E. Lin, Bellaire, TX (US); Kang Liu, Pearland, TX (US); Yongcheng Song, Pearland, TX (US); Fang-Tsyr Lin, Bellaire, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 14/921,914

(22) Filed: Oct. 23, 2015

(65) Prior Publication Data
US 2016/0113899 A1    Apr. 28, 2016

Related U.S. Application Data

(60) Provisional application No. 62/068,918, filed on Oct. 27, 2014.

(51) Int. Cl.
| | |
|---|---|
| A61K 31/365 | (2006.01) |
| A61K 31/704 | (2006.01) |
| A61K 33/24 | (2006.01) |
| C12Q 1/68 | (2006.01) |
| A61K 45/06 | (2006.01) |

(52) U.S. Cl.
CPC .......... *A61K 31/365* (2013.01); *A61K 31/704* (2013.01); *A61K 33/24* (2013.01); *A61K 45/06* (2013.01); *C12Q 1/6886* (2013.01); *C12Q 2600/158* (2013.01); *G01N 2333/99* (2013.01)

(58) Field of Classification Search
CPC .... A61K 45/06; A61K 31/365; A61K 31/704; A61K 33/24
See application file for complete search history.

(56) References Cited

PUBLICATIONS

Lulevich et al (J Phys Chem B. May 7, 2009; 113(18): 6511-6519).*
Trevigen Instruction (published 2011).*
Cancer Genetics (http://www.cancerindex.org/geneweb/TOPBP1.htm, accessed Oct. 21, 2016).*
Liu et al (Molecular and Cellular Biology, Nov. 2011, p. 4464-4481).*
The Human Protein Atlas (http://www.proteinatlas.org/ENSG00000163781-TOPBP1/cancer, accessed Oct. 30, 2017).*

* cited by examiner

*Primary Examiner* — Savitha Rao
*Assistant Examiner* — Angela Brown-Pettigrew
(74) *Attorney, Agent, or Firm* — VLP Law Group LLP; Kent H. Cheng

(57) ABSTRACT

The present invention provides a method of treating cancer that overexpresses TopBP1 by administering to a patient suffering from the cancer with an effective amount of a small molecule inhibitor that binds the BRCT7/8 domain of TopBP1.

3 Claims, 14 Drawing Sheets

US 9,636,323 B2

METHOD OF TREATING CANCER THAT OVEREXPRESSES TOPBP1

RELATED APPLICATIONS

This application claims priority from U.S. Provisional Patent Application Ser. No. 62/068,918, which was filed on Oct. 27, 2014.

BACKGROUND OF THE INVENTION

1. Field of the Invention

The present invention relates to treating cancer that overexpresses TopBP1 by administering to a patient suffering from the cancer with an effective amount of a small molecule inhibitor that binds the BRCT7/8 domain of TopBP1.

2. Description of the Related Art

Despite the complexity of mutations in different cancers, recent efforts in cancer genome sequencing project have shown a handful of core signaling pathways, such as receptor tyrosine kinases (RTK)/RAS/phosphatidylinositol 3-kinase (PI(3)K), p53 and retinoblastoma (Rb) protein, are deregulated in majority of solid tumors. For example, 77% of breast cancers have genetic alterations in PI(3)K/Akt pathway, and 49% have alterations in p53 signaling (see reference in (TCGA 2012)). Particularly in basal-like breast cancer (often triple-negative breast cancer or TNBC), 84% show TP53 mutations, 35% show PTEN mutation/loss and 20% show RB1 mutation/loss (see reference in (TCGA 2012)). These deregulated signaling pathways often converge to some common modulators.

As a key regulator for cell growth, the Rb pathway is de-regulated in most cancers, resulting in high E2F1 activities to drive cell cycle progression. E2F1 also has a pro-apoptotic role through activating target genes such as p73 (Irwin et al. 2000; Stiewe and Putzer 2000), Apaf-1, and caspases (Muller et al. 2001; Nahle et al. 2002) during DNA damage (Lin et al. 2001). How to activate E2F1 pro-apoptotic activity inside cancer cells remains an elusive goal. Previously, we showed that a checkpoint activator protein, TopBP1 (topoisomerase IIβ-binding protein 1), plays a critical role in suppressing E2F1 pro-apoptotic activity in response to PI(3)K/Akt signaling, which suggests TopBP1 as a therapeutic target to activate E2F1-dependent apoptosis in cancer (Liu et al. 2003; Liu et al. 2004; Liu et al. 2006; Liu et al. 2013).

TopBP1 utilizes its multiple BRCA1 carboxyl-terminal (BRCT) motifs as scaffolds to modulate many processes of DNA metabolism; such as DNA damage checkpoint, replication, and transcription (Garcia et al. 2005). TopBP1 represses E2F1 transcriptional activities by recruiting Brg1/Brm chromatin remodeling complex (Liu et al. 2004). TopBP1 also binds the DNA-binding domain (DBD) of p53 to inhibit its transcriptional function (Liu et al. 2009). Regulation of E2F1 and p53 by TopBP1 is important to control the pro-apoptotic activities of both transcription factors during normal S phase transition. While TopBP1 is involved in seemingly separate functions, our recent study showed that its functions in replication checkpoint and transcriptional regulation are indeed coordinated via an Akt-dependent conformational change of TopBP1 (Liu et al. 2013). Akt phosphorylates TopBP1 at Ser1159 and induces its oligomerization through an intermolecular interaction between the phosphorylated Ser1159 residue (pS1159) and the $7^{th}$-$8^{th}$ BRCT (BRCT7/8) domain of two TopBP1 molecules (Liu et al. 2006; Liu et al. 2013). Oligomerization of TopBP1 then induces its binding to E2F1, but at the same time prevents its recruitment to chromatin and ATR binding and perturbs its checkpoint-activating functions (Liu et al. 2013). Thus, by regulating TopBP1 quaternary structure, Akt switches TopBP1 function from checkpoint activation to transcriptional regulation. This mechanism is responsible for inhibition of E2F1-dependent apoptosis (an oncogenic checkpoint) and inhibition of ATR function (replication checkpoint) in the tumors with high Akt activity. Therefore, selective blockade of TopBP1 oligomerization may provide a novel therapeutic strategy in cancer cells which exhibit up-regulated PI3K/Akt signaling.

Many mutant p53 (mutp53) proteins do not only lose normal p53 function, but also gain new functions which contribute to cancer progression ("gain of function" activities (GOF)) (Freed-Pastor and Prives 2012; Muller and Vousden 2013). In addition to mutations, cancer cells can have a different mechanism to inactivate p53: up-regulation of p53 negative regulators, such as MDM2 (Manfredi 2010), MDMX (Marine et al. 2006) and TopBP1 (Liu et al. 2009). Adding to the complexity of p53 regulation is the presence of 12 p53 isoforms with differential expression (Khoury and Bourdon 2011), some of which have dominant-negative activities against p53 (Bourdon et al. 2005).

TopBP1 also mediates mutp53 GOF by facilitating its complex formation with NF-Y and p63/p73 (Liu et al. 2011). Since TopBP1 is an E2F target (Liu et al. 2004), it is often up-regulated upon inactivation of the Rb pathway (Liu et al. 2009). Indeed, TopBP1 is frequently overexpressed in breast cancer and its overexpression is associated with a shorter survival (Liu et al. 2009; Liu et al. 2011). SNPs in TopBP1 that cause higher expression of TopBP1 mRNA and protein have also been associated with an increased risk in breast and endometrial cancers (Forma et al. 2013a; Forma et al. 2013b). Thus, deregulation of the Rb pathway may be functionally linked to mutp53, and be responsible for at least part of mutp53 GOF via TopBP1. The accumulated TopBP1 in cancer cells then inhibits growth checkpoints through repressing E2F1 and p53 functions, and collaborates with mutp53 to further promote tumor progression. Therefore, TopBP1 might be a target among the nexus of these major oncogenic pathways. Here we perform a molecular docking screening and identify calcein as a compound to target the BRCT7/8 domain of TopBP1. We also use its cell-permeable derivative Calcein AM to provide proof-of-principle evidence for targeting TopBP1 as a cancer therapy.

SUMMARY OF THE INVENTION

We identify a lead compound targeting C-terminal BRCT domains of TopBP1, and provide evidence to support TopBP1 as a novel cancer therapeutic target that functions in a convergent point of multiple oncogenic pathways: inactivation of Rb pathway leads to its overexpression, and activation of RTK/RAS/PI(3)K induces its phosphorylation. The accumulation of phosphorylated TopBP1 in cancer cells may cause defects in growth checkpoints through repressing E2F1 and p53 functions, and turning mutp53 into oncoproteins (FIG. 10b). Using a small molecule inhibitor capable of blocking the endogenous interactions between TopBP1 and E2F1 as well as mutp53, we validate TopBP1 as a therapeutic target in the tumors to activate E2F1 pro-apoptotic activity and to avert the oncogenic activity of mutp53. While the cytotoxic activity of Calcein AM against cancer cells was noticed before, we now identify its in vivo target and elucidate its selective anti-tumor activity through a novel TopBP1-dependent mechanism of action. Finally, for the first time we demonstrate Calcein AM antitumor activity in two breast cancer xenograft models. While drug development typically aims at upstream receptors/kinases, our study provides evidence for targeting the proteins in the nexus of multiple signaling pathways as new cancer therapeutics.

Different mutant p53 proteins may have different functions. TopBP1 can bind to several hot-spots mutants, including both DNA contact mutant (such as R273H) and conformational mutants (such as R175H and R249S) (Liu et al. 2011). Consistently, by targeting TopBP1, Calcein AM releases p73 from mutp53(R273H) in MDA-MB468 cells and from mutp53(R249S) in BT549 cells. Although the effect of Calcein AM against each mutant p53 will need to be tested experimentally, the two examples presented here suggest that Calcein AM might be used to treat cancer cells harboring a broad spectrum of p53 mutations. In BT549 cells, we demonstrated a role for E2F1 and p63/p73 for mediating Calcein AM-induced apoptosis (FIG. 7). TopBP1-BRCT7/8 also binds to other transcription factors, such as Miz1 (Herold et al. 2002; Liu et al. 2006). In fact, Calcein AM treatment also released Miz1 from TopBP1 (FIG. 2f), suggesting that Miz1 might also contribute to the toxic effects of Calcein AM. The other factor worth considering is the difference in genetic alterations causing Akt activation in cancer. PTEN loss mainly occurs in basal-like breast cancer, whereas PIK3CA mutations are more common in luminal or Her2E subtypes breast cancer (see reference in (TCGA 2012)). Both MDA-MB468 and BT549 cell lines tested here have PTEN loss. Whether cancer cells with PIK3CA mutations respond differently to Calcein AM will be tested in the future. According to NCI-60 cell lines database, a PIK3CA mutant (H1047R) cell line T47D still responds to Calcein AM ($GI_{50}$ 1.4 µM) (FIG. 6a).

Calcein AM has been considered to be non-toxic to a wide spectrum of cell types esp. in normal cells, thus is widely used for viability assay and in vivo physiological cell marking. The fact that the mice injected with Calcein AM did not manifest any apparent toxicity in our study indicates that the dose (40 mg/kg) that is effective in shrinking MDA-MB468 xenografts is quite tolerable for the mice. Consistently, the toxicology study of Calcein AM performed by Dojindo Laboratories shows that oral LD50 in rats is 14.5 g/kg; oral LD50 in mice is 17 g/kg; percutaneous LD50 in mice is 5 g/kg (according to Material Safety Data Sheet, http://www.dojindo.com/store/p/162-Cellstain-Calcein-AM-Solution.html). On the other hand, calcein may bind ions such as Ca and Mg, thus the potential effects of ion chelation need to be considered. However, it only binds these ions at strong alkaline pH (therefore it is now rarely used as intracellular Ca indicator). A more potent intracellular calcium chelator BAPTA/AM in fact has a neuroprotective effect by preventing the cell damage caused by elevated cytoplasmic Ca levels (Collatz et al. 1997) during cerebral ischemia. Moreover, the cytotoxicity of Calcein AM in cancer cells that we observed depends on TopBP1, and Calcein AM treatment induces E2F1 and mutp53 target gene changes. Thus, it is unlikely that the cytotoxicity is caused by calcium chelation. Another potential property of Calcein AM warrants consideration is its sensitivity to ROS (reactive oxygen species). After removal of the acetomethoxy side chain, calcein can be oxidized and becomes fluorescent. Thus it was proposed to be used as a detector of intracellular oxidative activity (Uggeri et al. 2004). However, the ROS-sensitive fluorescein derivatives do not produce oxidative damage (instead they recycle ROS), therefore are used to detect intracellular ROS generation in living cells (Molecular Probes™). Lack of pS15-p53 signal after Calcein AM treatment (see Supplementary FIG. 9 in (Chowdhury et al. 2014)) also indicates that it does not produce oxidative damage or DNA damage.

TopBP1 protein is overexpressed in nearly 60% (46 out of 79 cases) of primary breast cancer tissues when compared with matched uninvolved breast tissues by Western and IHC analyses (Liu et al. 2009). An increased risk of breast cancer relapse or death is seen in patients with tumors containing high levels of TopBP1 protein (Liu et al. 2009) or TopBP1 RNA (analysis of four breast databases composed of 1028 patients (Liu et al. 2011)). Activation of PI(3)K/Akt signaling occurs in 77% of breast cancer (see reference in (2012)). Thus, this convergent event is expected to be quite prevalent in breast cancer, particularly in TNBCs which overexpress TopBP1 in nearly all cases (Liu et al. 2009) and harbor mutp53 in 84% of cases (see reference in (TCGA 2012)). Therefore, the impact of this novel therapy would be very significant for many breast cancer patients. Since these oncogenic pathways are common to many cancers. For example, the genetic alterations in glioblastoma occur mainly in these three signaling pathways: RTK/RAS/PI(3)K (88%), p53 (87%) and Rb (78%) (see reference in (TCGA 2008)). Mutations in p53 and PI3K/Akt pathways are among the most frequent genetic abnormalities in all cancers and are strongly associated with poor prognosis, and resistance to therapy. Hence, the anti-TopBP1 therapy might be applicable to many other types of cancers.

Accordingly, the present invention provides a method of treating cancer that overexpresses TopBP1 by administering to a patient suffering from the cancer with an effective amount of a small molecule inhibitor that binds the BRCT7/8 domain of TopBP1.

The small molecule inhibitor may be Calcein or Calcein AM. The cancer that overexpresses TopBP1 may be identified by immunohistochemistry, immunoblotting or measurement of TopBP1 mRNA levels by quantitative RT-PCR (reverse transcription-polymerase chain reaction). See, for example, K. Liu, et al. (Liu et al. 2009), "Regulation of p53 by TopBP1: a Potential Mechanism for p53 Inactivation in Cancer," Molecular and Cellular Biology, May 2009, pages 2673-2693. The effective amount of the small molecule inhibitor that binds the BRCT7/8 domain of TopBP1 and blocks its functions can be determined by pS1159 peptide binding and GST-p53(DBD) pulldown assays. In the case where Calcein is used, it appears that the effective amount of Calcein that needs to be present is 60-300 nM. See FIG. 1, f and g.

In one embodiment of the inventive method of treating cancer that overexpresses TopBP1, the cancer to be treated is selected from the group consisting of breast cancer, ovarian cancer, leukemia, lung cancer, multiple myeloma, hepatoma and gliobastoma multiforme.

In another embodiment, the method of treating cancer that overexpresses TopBP1 further comprises the step of administering to the patient a chemotherapeutic agent.

In another embodiment, the invention provides a method of sensitizing cancer cells to a chemotherapeutic agent in a patient suffering from cancer by administering an effective amount of a small molecule inhibitor that bind the BRCT7/8 domain of TopBP1. The small molecule inhibitor may be selected from the group consisting of Calcein and Calcein AM. The chemotherapeutic agent may be doxorubicin or cisplatin.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

(c) The effect of Calcein AM (2.5 μM) on the doxorubicin sensitivity in MCF10A and MDA-MB468 cells lines. MTS assays were performed 5 h after treatment. The 490 nm absorbance readings were normalized to the "0 μM Doxorubicin" controls within each group. The MTS readings normalized to the "DMSO, 0 μM-Doxorubicin" control cells are presented in Supplementary FIG. 5 in paper (Chowdhury et al. 2014). Shown are means±S.D. derived from three biological replicates. P<0.001 compared with DMSO control.

(d) MDA-MB468 cells were seeded into an Ultra-low Adherent 6-well plate with complete MammoCult™ medium, and then cultured for 11 days in DMSO or Calcein AM (2.5 μM). The mammospheres were observed at 10× magnification. The diameters of 15 mammospheres were measured from three independent culture experiments using a Zeiss digital inverted microscope (Axio Observer). *, P<0.001 (two-tailed t test). Higher-magnification images are shown in Supplementary FIG. 6 (Chowdhury et al. 2014).

(e) MDA-MB468 cells were treated with DMSO or increasing doses of Calcein AM for 16 h. Cells were then grown in fresh media without Calcein AM for eight more days and then stained with crystal violet. Each treatment was performed in triplicate. Representative images are shown in the left panels (a complete set of data are shown in Supplementary FIG. 7 (Chowdhury et al. 2014)). Colonies were counted and colony numbers relative to DMSO controls (means±S.D.) are shown in the right graph. *, P<0.001 compared with DMSO controls (two-tailed t test).

(f) In parallel with the experiment in (e), some MDA-MB468 cells were treated with DMSO or increasing doses of Calcein AM for 16 h, and then assayed for caspase activation. Shown are means±S.D. derived from three biological replicates. *, P<0.001, compared with DMSO control (two-tailed t test).

Figure 5:
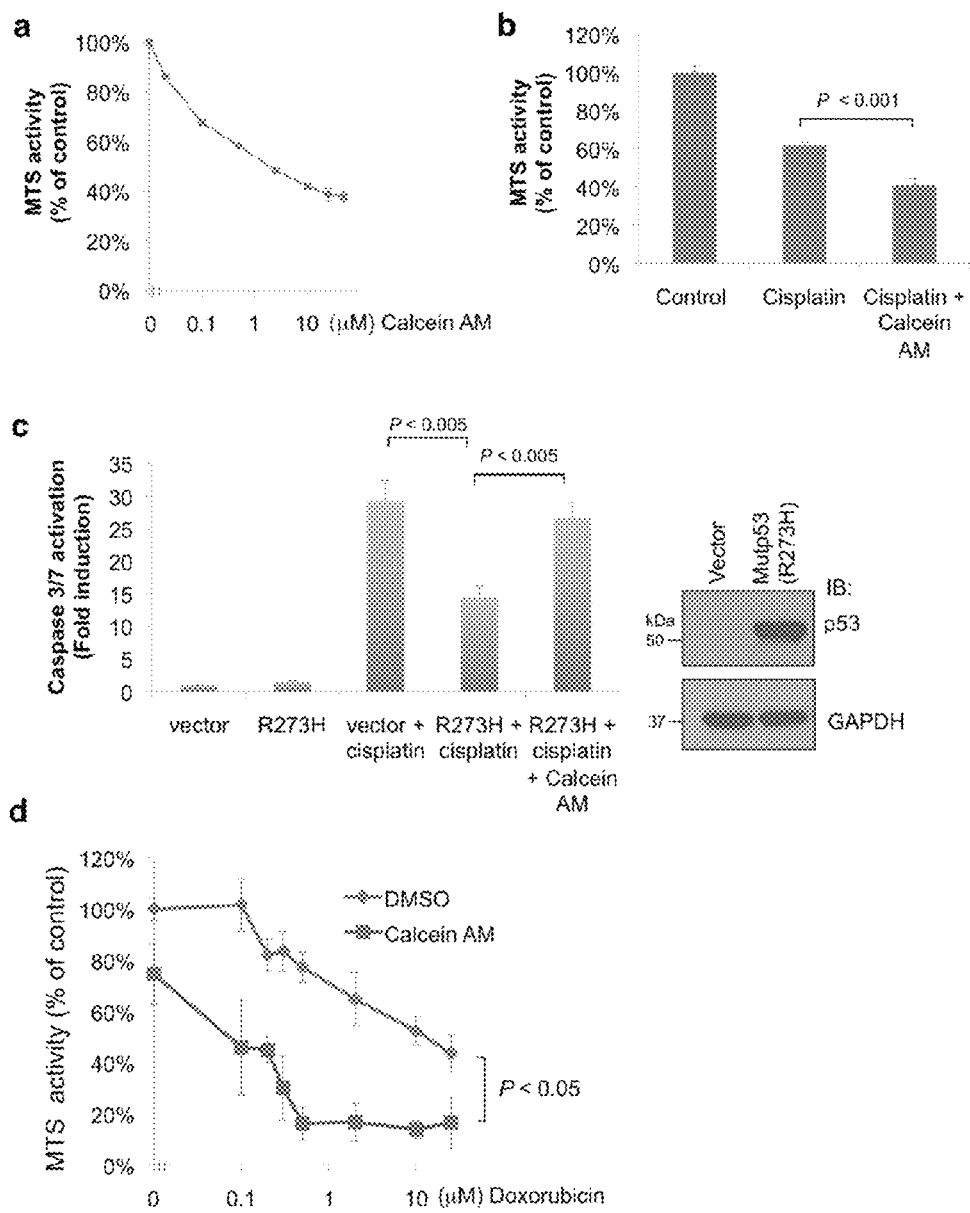

FIG. 5 Calcein AM sensitizes mutp53-harboring cancer cells to chemotherapy.

(a) Cell viability was measured by MTS assay in an ovarian cancer cell line SKOV-3 with increasing concentrations of Calcein AM for overnight.

(b) SKOV-3 cells were treated with cisplatin (20 μM) alone or with Calcein AM (5 μM) for 20 h, and then subjected to MTS assay.

(c) SKOV-3 cells (p53-null) were transfected with an empty vector control or mutp53(R273H) and then treated with cisplatin (20 μM) alone or with Calcein AM (5 μM) for 20 h. Apoptosis was measured by Caspase-Glo 3/7 activity assay. Expression of mutp53 was confirmed by Western blot analysis (right panel).

(d) RPMI 8226 cells were treated with an increasing dose of doxorubicin along with vehicle (DMSO) or with Calcein AM (2.5 μM) for 12 h before subjecting to MTS assay. Each treatment was tested in triplicate, and the values were normalized to vehicle control wells. Results shown in (a), (b), (c) and (d) are means±S.D. derived from three biological replicates. P values are for two-tailed t test.

Figure 6:
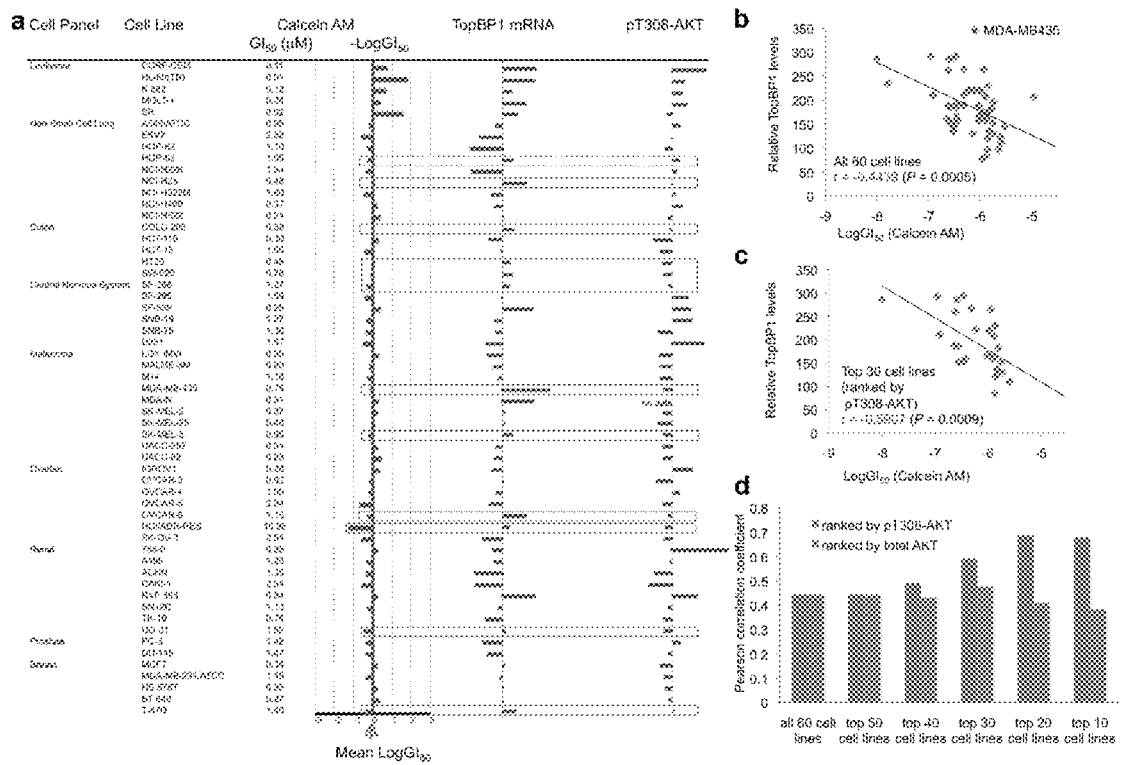

FIG. 6 Calcein AM sensitivity correlates with TopBP1 expression and Akt activity in NCI-60 cancer cell lines.

(a) The sensitivity to Calcein AM (NSC 689290) and TopBP1 mRNA levels (GC181500) and pT308-AKT levels by RPPA (MT18349) in NCI-60 cell lines were extracted from NCI-DTP server. Box lines highlight the cell lines with discrepancy in Log $GI_{50}$ and TopBP1 mRNA levels. Most of the discrepancy was found in cells with low pT308-AKT levels except HOP-92 cells (dotted box).

(b) The correlation between the sensitivity of NCI-60 cell lines to Calcein AM (expressed as Log $GI_{50}$, the concentration that causes 50% growth inhibition) and TopBP1 RNA levels in these cell lines. Pearson correlation coefficient (r) and P value are shown.

(c) Only the top 30 cell lines with a higher level of pT308-AKT are included in this correlative analysis.

(d) The NCI-60 cell lines were ranked according to either pT308-AKT or total AKT expression levels followed by the correlative analysis with TopBP1 expression for the selected cell lines.

Figure 7:
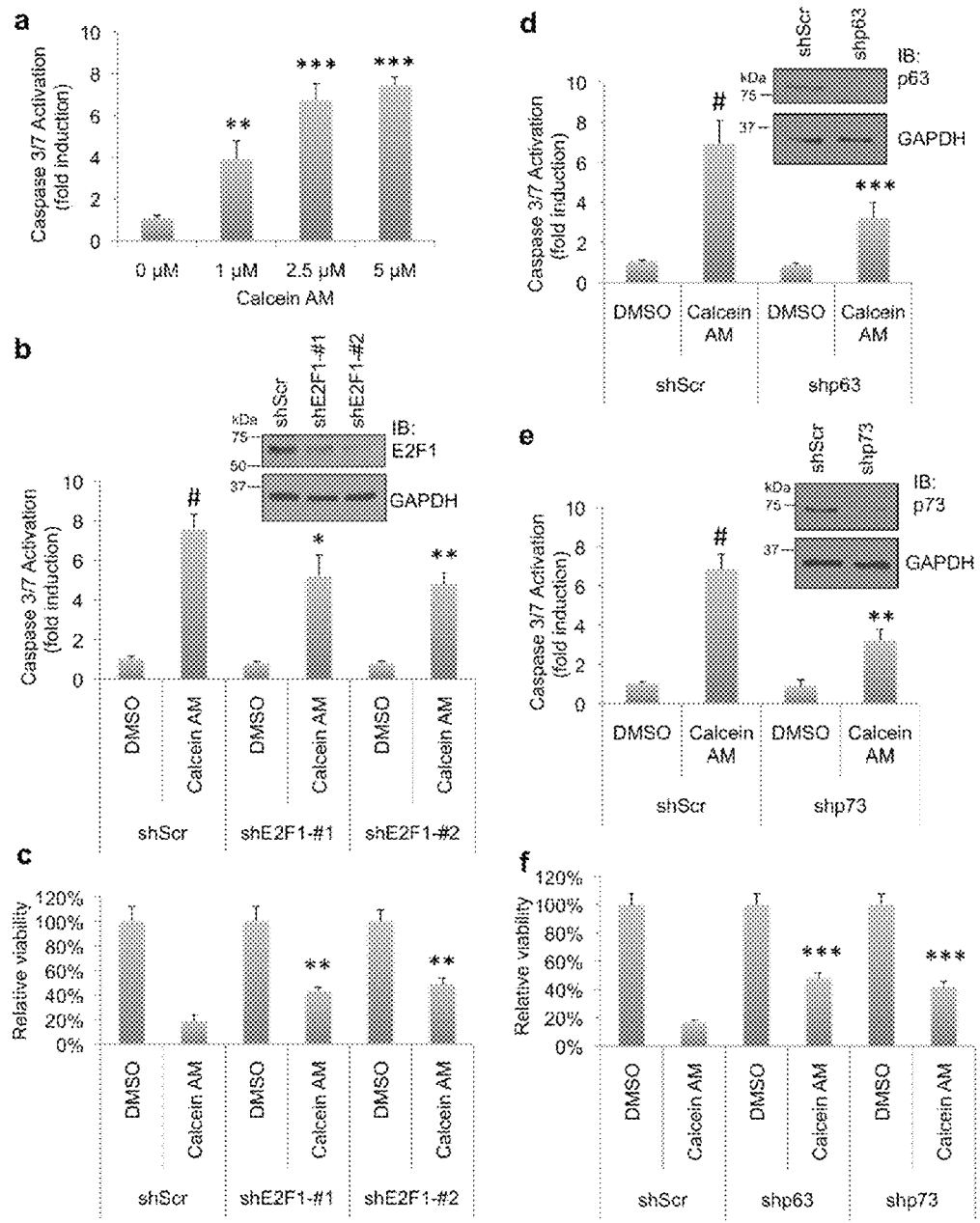

FIG. 7. The cytotoxicity of Calcein AM in cancer cells depends on E2F1 and p63/p73.

(a) BT549 cells were treated with Calcein AM at indicated concentrations for 16 h. Apoptosis was then analyzed by Caspase-Glo 3/7 activity assay. Shown are means±S.D. derived from three biological replicates. , P<0.01; *, P<0.001, compared with DMSO control (two-tailed t test).

(b) BT549 cells were transfected with two shRNAs against E2F1 or a scrambled (Scr) shRNA. 48 h after transfection, cells were treated with Calcein AM (2.5 μM) for 16 h and then subjected to Caspase-Glo 3/7 activity assay. Shown are means±S.D. derived from three biological replicates. #, P<0.001 compared with DMSO group; *, P<0.05; **, P<0.01, compared with shScr-Calcein AM group (two-tailed t test). Depletion of E2F1 in these samples was confirmed by Western blot analysis (right panels).

(c) BT549 cells were transfected with two shE2F1 as in (b), and then treated with Calcein AM (2.5 μM) or DMSO for 20 h. Total number of living cells was counted by trypan blue exclusion assay and normalized to the vehicle controls. Shown are means±S.D. derived from three biological replicates. **, P<0.005 compared with shScr-Calcein AM group (two-tailed t test).

(d) BT549 cells were transfected with shRNA against p63 or a scrambled (Scr) shRNA. 48 h after transfection, cells were treated with Calcein AM (2.5 μM) for 17 h and then subjected to Caspase-Glo 3/7 activity assay. Shown are means±S.D. derived from five biological replicates. #, P<0.001 compared with DMSO group; ***, P<0.001 compared with shScr-Calcein AM group (two-tailed t test). Depletion of p63 was confirmed by Western blot analysis (upper panels).

(e) The expression of p73 in BT549 was depleted by transfecting shRNA against p73. Two days later, cells were treated with Calcein AM (2.5 μM) for 17 h and then subjected to Caspase-Glo 3/7 activity assay. Shown are means±S.D. derived from three biological replicates. #, P<0.001 compared with DMSO group; **, P<0.01 compared with shScr-Calcein AM group (two-tailed t test). Depletion of p73 was confirmed by Western blot analysis (upper panels).

(f) BT549 cells were transfected with shp63 or shp73 as in (d) and (e), and then treated with Calcein AM (2 μM) or DMSO vehicle for 15 h. The number of viable cells was counted by trypan blue exclusion assay and normalized to the vehicle controls. Shown are means±S.D. derived from three biological replicates. The result was replicated two times. ***, P<0.001 compared with shScr-Calcein AM group (two-tailed t test).

Figure 8:
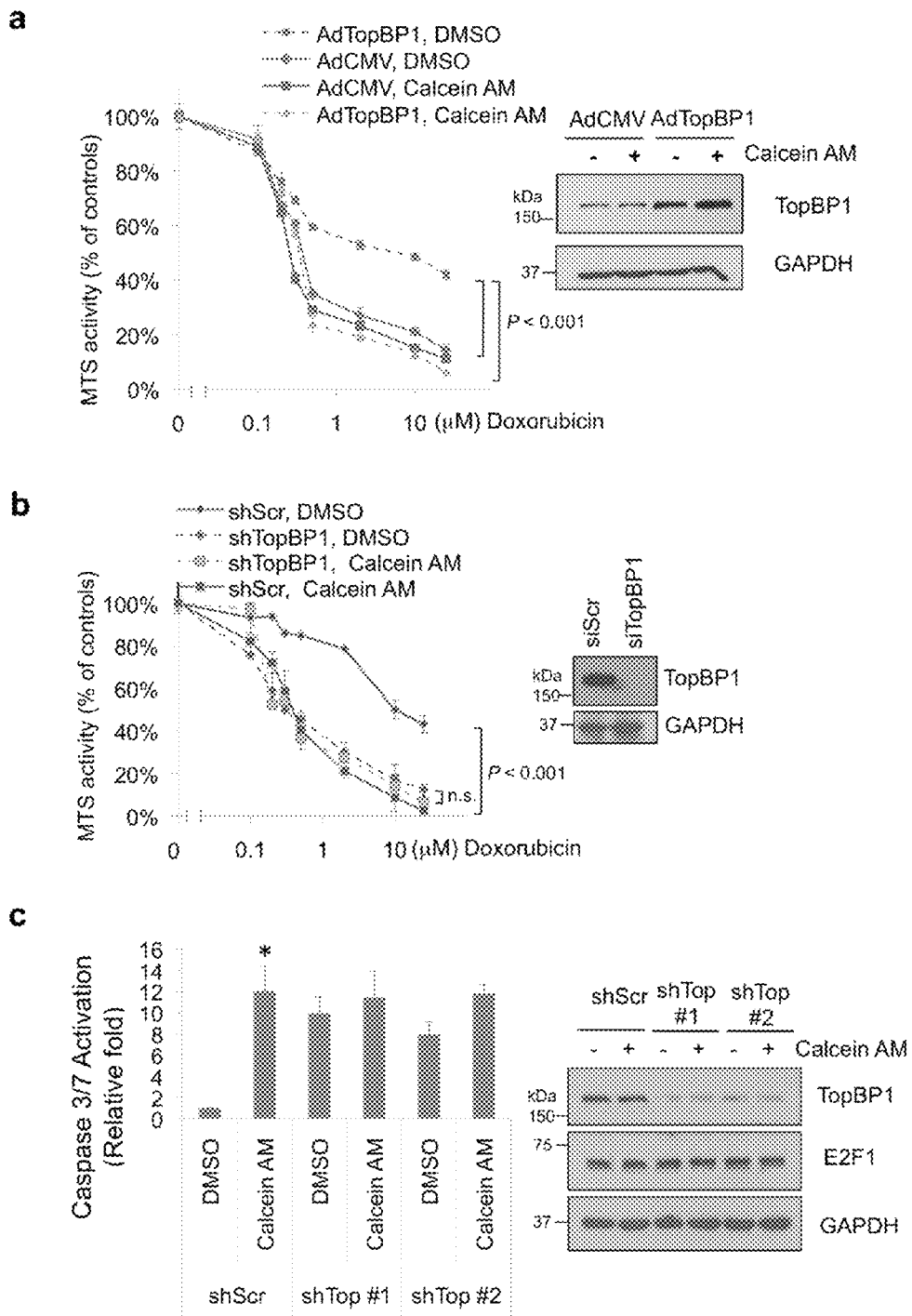

FIG. 8 The sensitivity to Calcein AM in cancer cells depends on TopBP1.

Figure 4:
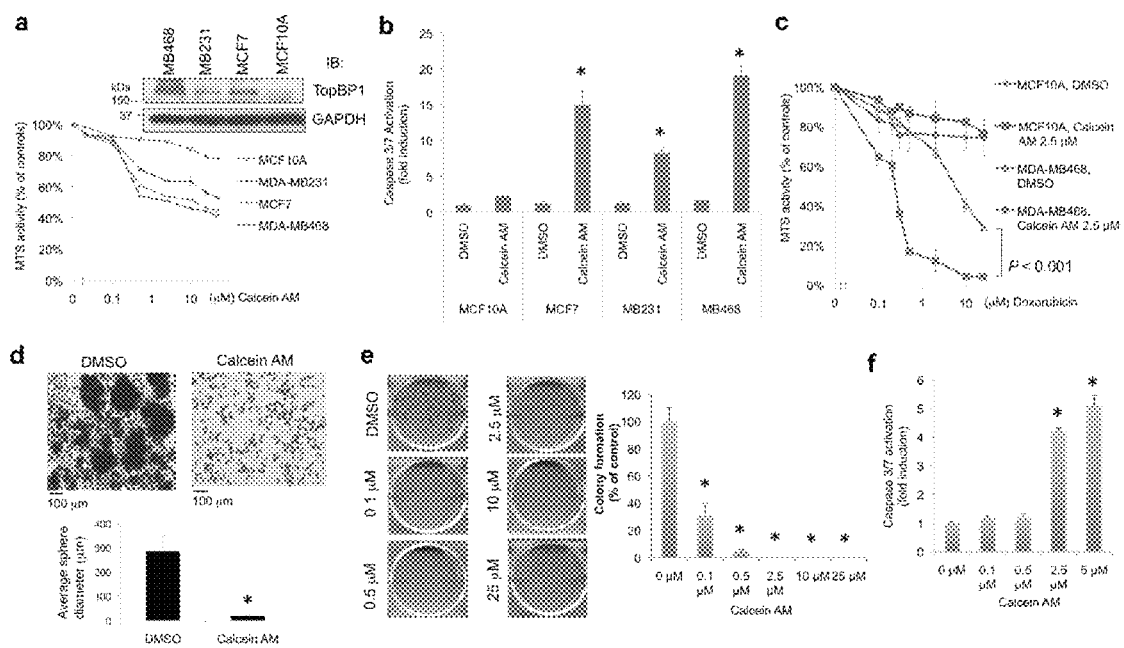
FIG. 4 Calcein AM shows anti-tumor activity against many different cancer cell lines.
  (a) MTS assays were performed in breast cancer cell lines MDA-MB468, MDA-MB231 and MCF7, and non-transformed breast epithelial cell line MCF10A with increasing concentrations of Calcein AM for 5 h. The data represent means±S.D. (n=3 biological replicates). The immunoblot showed the TopBP1 expression levels in these four cell lines (upper panel).
  (b) Cells were treated with Calcein AM (2.5 µM) overnight and then subjected to Caspase-Glo 3/7 activity assay. Shown are means±S.D. derived from three independent experiments. *, P<0.001, compared with DMSO control (two-tailed t test).

(a) MDA-MB231 cells were infected with recombinant adenoviruses expressing empty vector (AdCMV) or AdTopBP1 (multiplicity of infection 500). After two days, the sensitivity to doxorubicin in the presence of DMSO or Calcein AM (2.5 µM) was measured as in FIG. 4c. Shown are means±S.D. from three biological replicates. TopBP1 overexpression was confirmed by Western blotting (right panel). The 490 nm absorbance readings were normalized to the "0 µM Doxorubicin" controls within each group. The MTS readings normalized to the "DMSO, 0 µM-Doxorubicin" control cells are presented in Supplementary FIG. 8a (Chowdhury et al. 2014).

(b) Doxorubicin sensitivity was assayed in TopBP1-depleted MDA-MB468 cells treated with doxorubicin and either DMSO or Calcein AM (2.5 µM) for 5 h and then subjected to MTS assay. Shown are means±S.D. from three biological replicates. TopBP1 knockdown was confirmed by Western blotting (right panel). n.s.: not significant. The MTS readings are relative to the "0 µM Doxorubicin" controls of each group. The MTS readings normalized to the "DMSO, 0 µM-Doxorubicin" control cells are presented in (Chowdhury et al. 2014) Supplementary FIG. 8b.

(c) HEK293 cells transfected with pSuper-shScr or two different pSuper-shTopBP1 constructs (shTop #1 and #2) (Liu et al. 2004) were treated with 2.5 µM Calcein or DMSO overnight. Apoptosis was measured by Caspase-Glo 3/7 activity assay. *, P=0.001, compared with shScr control group (two-tailed t test, n=3 biological replicates). E2F1 expression and depletion of TopBP1 were shown by immunoblotting (right panel).

Figure 9:
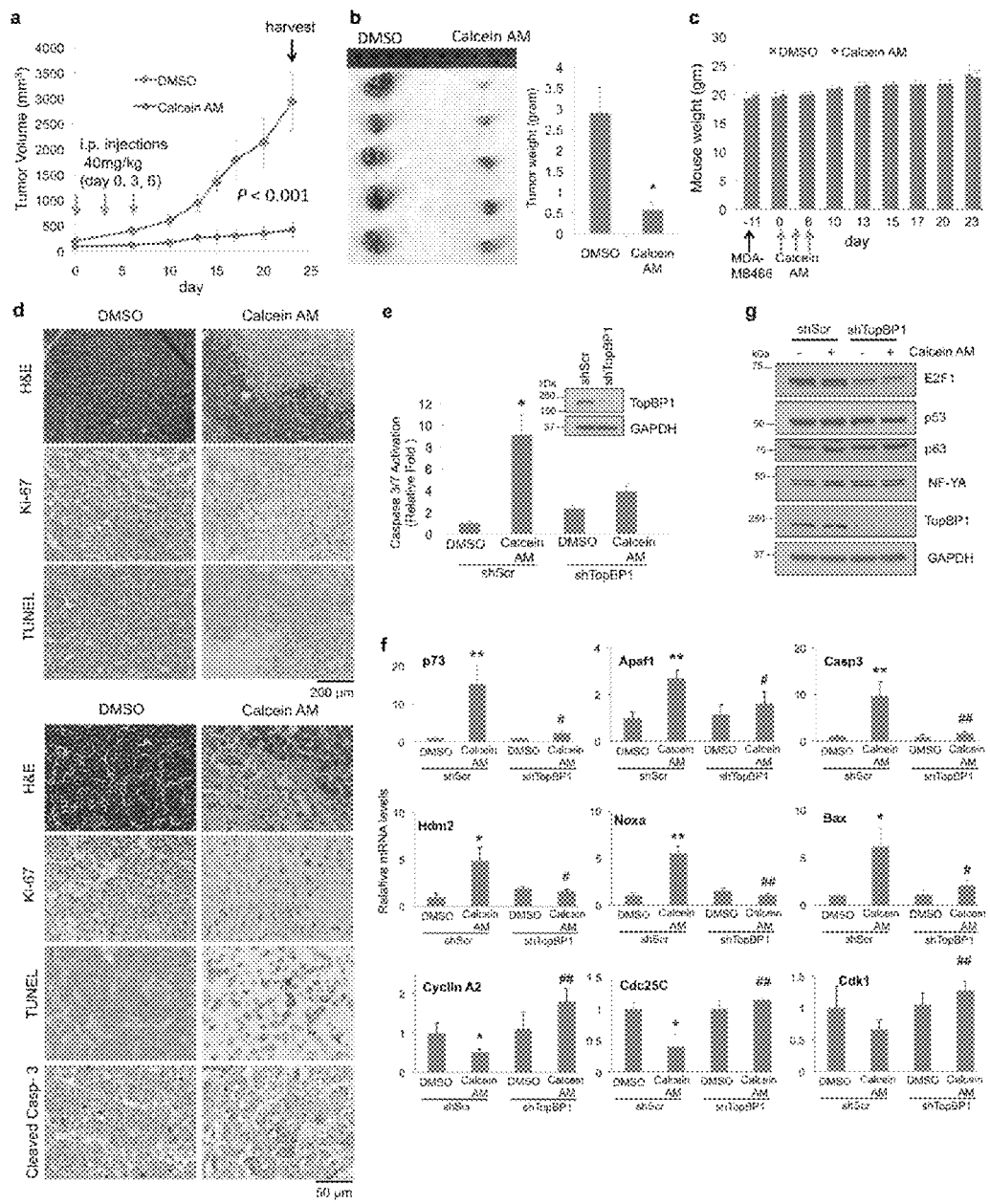

FIG. 9 Effect of Calcein AM on tumor growth in the MDA-MB468 xenograft model and impact of TopBP1 on Calcein AM response in cultured MDA-MB468 cells.

(a) Nude mice bearing MDA-MB468 xenografts were administered with Calcein AM or vehicle DMSO via i.p. injection. Mean tumor volumes±S.D. are shown; n=5 mice per group. This result was replicated, and shown in (Chowdhury et al. 2014) Supplementary FIG. 11.

(b) Photographs of the MDA-MB468 xenograft tumors (left), and tumor weights (right).). *, P<0.001 (two-tailed t test).

(c) Mean mouse body weights±S.D. (n=5) from the injection of MDA-MB468 cells (day −11).

(d) Representative images of H&E, Ki-67 immunohistochemical staining and TUNEL staining of xenografts at 10× magnification (upper panels). Representative images of H&E, Ki-67, TUNEL, and cleaved caspase-3 staining at 40× magnification (lower panels).

(e) The effect of Calcein AM in MDA-MB468 cells depended on TopBP1. TopBP1-depleted MDA-MB468 cells were treated with Calcein AM (2.5 µM) overnight and then subjected to Caspase-Glo 3/7 activity assay. siScr: scrambled RNAi control. *, P=0.002, compared with siScr/DMSO, P=0.01 compared with siTopBP1/Calcein AM (two-tailed t test, n=3). Depletion of TopBP1 was verified by Western blot analysis (upper panel).

(f) TopBP1-depleted and the siScr control MDA-MB468 cells were treated with Calcein AM (2.5 µM, 5 h), and E2F1, p53 and NF-Y target gene expression was analyzed by qRT-PCR as in FIG. 3d. **, P<0.01, *, P<0.05, compared with DMSO samples; ##, P<0.01, #, P<0.05, compared with siScr/Calcein AM samples (two-tailed t test). The data represent means±S.D. (n=3).

(g) Aliquots of the cell lysates in (f) were analyzed for Western blotting.

Figure 10:
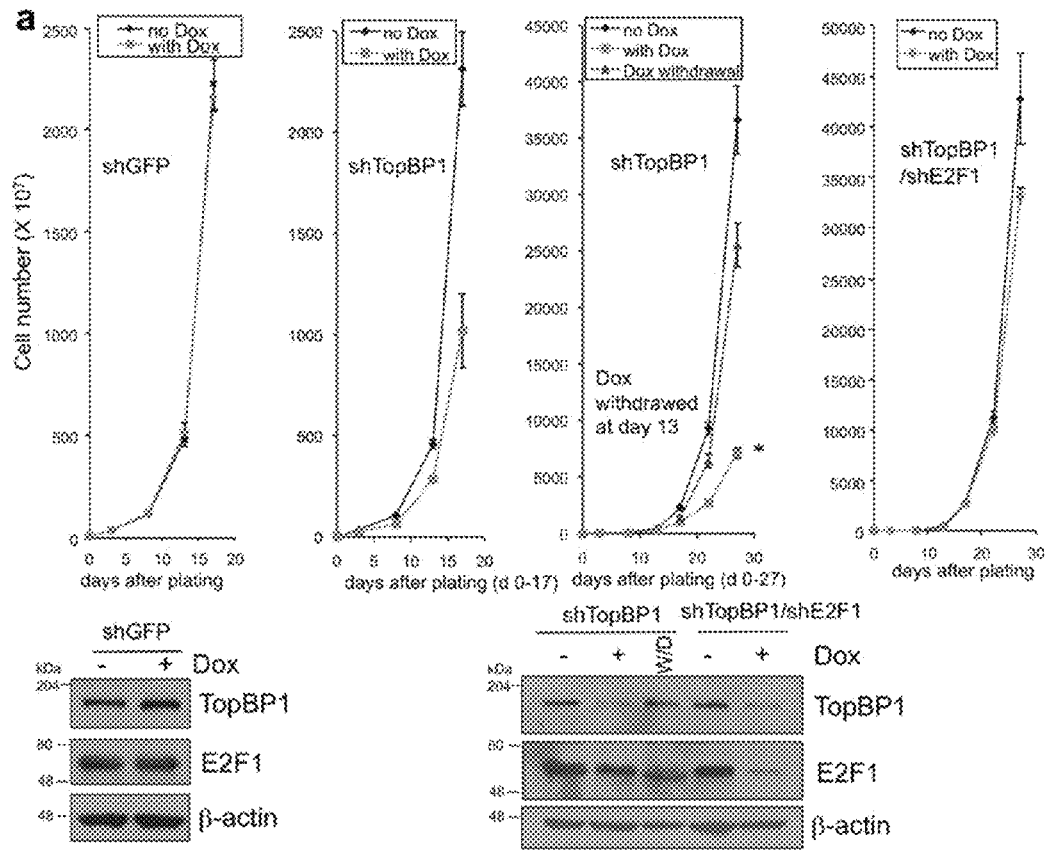
Figure 10:
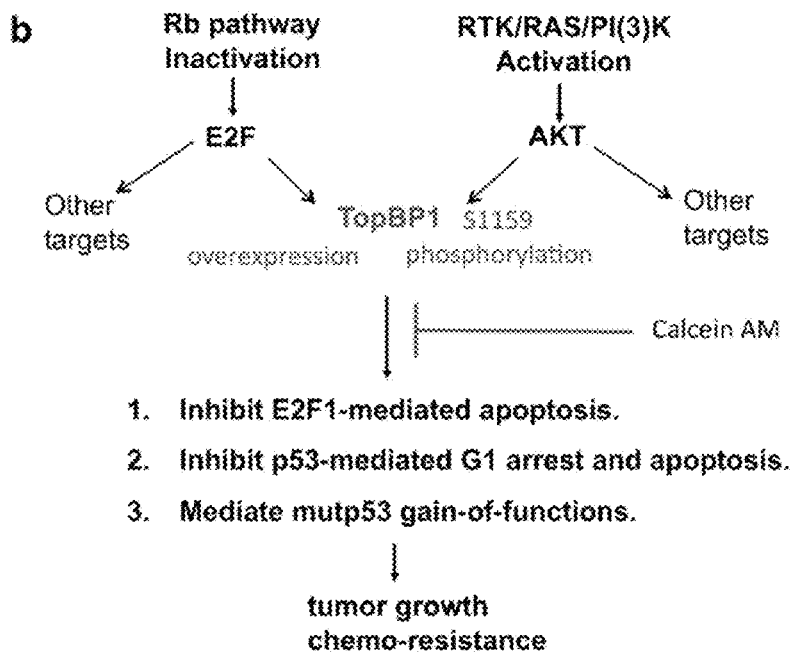

FIG. 10 Role of E2F1 in mediating growth suppression upon TopBP1 depletion and a scheme summarizing the present studies.

(a) The decrease in cell number upon TopBP1 depletion is in part dependent on E2F1. We first established U2OS stable cell lines for doxycycline-inducible expression of control shGFP, shTopBP1, and both shTopBP1 and shE2F1 using T-REX system (Yang et al. 2008; Liu et al. 2009; Wang et al. 2010). ShRNAs were then induced with doxycycline (DOX) on day 0 (pink lines), and cells were counted by a Beckman Coulter counter. An aliquot of DOX-treated shTopBP1 cells were plated in medium without doxycycline (Dox withdrawal, W/D) since day 13 (third graph from the left, Dox withdrawal, green line). To make it easy to compare, day 0-17 of shTopBP1 was plotted (second graph from the left) for comparison with shGFP, and day 0-27 of shTopBP1 was plotted (third graph from the left) for comparison with shTopBP1/shE2F1. The data represent means±S.D. from three biological replicates. *, P<0.001 when compared with "no Dox", and P<0.01 when compared with "Dox withdrawal" (two-tailed t test). Lower panels: Western blots of TopBP1 and E2F1.

(b) TopBP1 is at a convergent point between Rb and PI(3)K signaling pathways and contributes to tumor progression through E2F1 and p53 regulation. Its action is blocked by Calcein AM.

Figure 11:
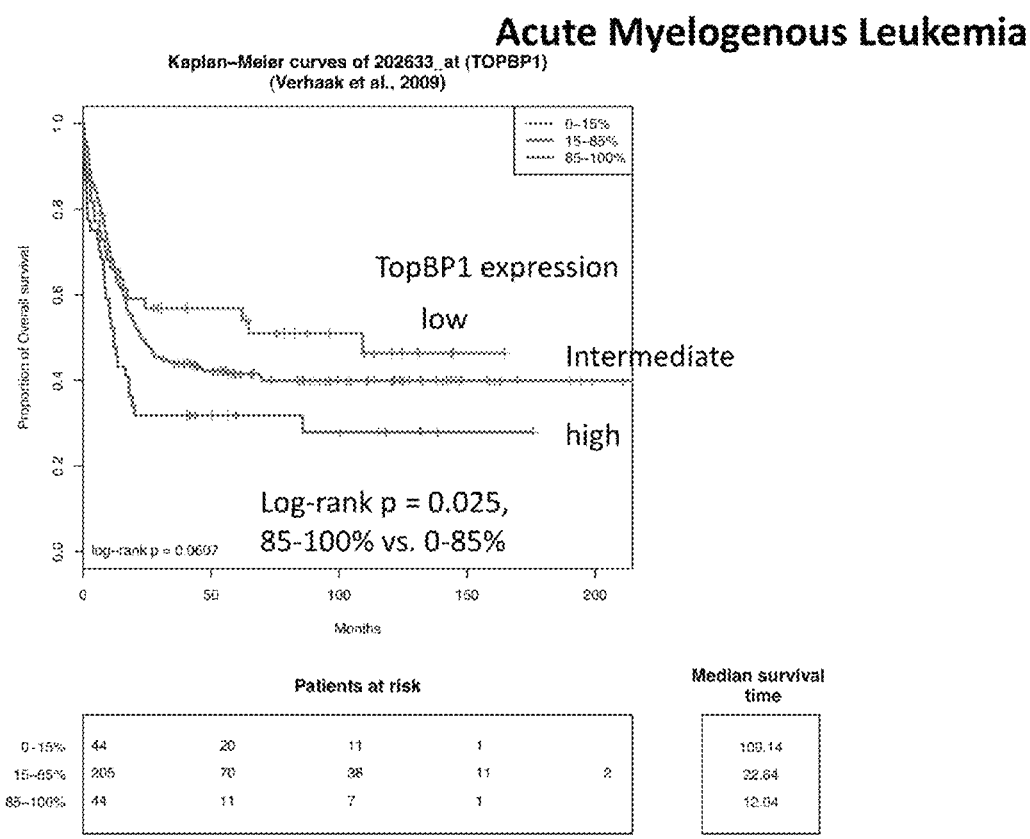

FIG. 11 High TopBP1 expression in acute myelogenous leukemia (AML) patients is associated with a poor prognosis.

The expression of TopBP1 in AML samples and patients' overall survival from a database (Verhaak et al. 2009) are analyzed. All patients were first ranked according to their TopBP1 expression in leukemia samples, and then grouped to three groups: 1. low TopBP1 expression group (the bottom 0-15% of the patients), 2. intermediate TopBP1 expression group (15-85%), and 3. high TopBP1 expression group (the top 85-100% of the patients).

Figure 12:
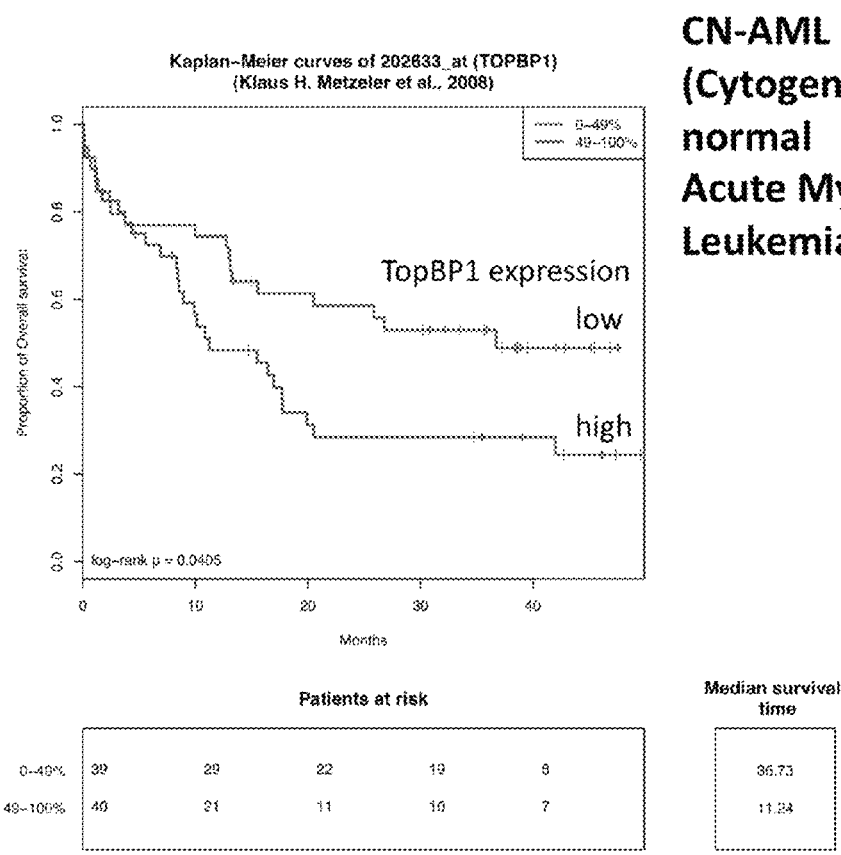

FIG. 12 High TopBP1 expression in cytogenetically normal-acute myelogenous leukemia (CN-AML) patients is associated with a shorter survival.

The expression of TopBP1 in CN-AML samples and patients' overall survival from a database (Metzeler et al. 2008) are analyzed. All patients were first ranked according to their TopBP1 expression in leukemia samples, and then grouped to two groups: 1. low TopBP1 expression group (the bottom 0-49% of the patients), and 2. high TopBP1 expression group (the top 49-100% of the patients).

Figure 13:
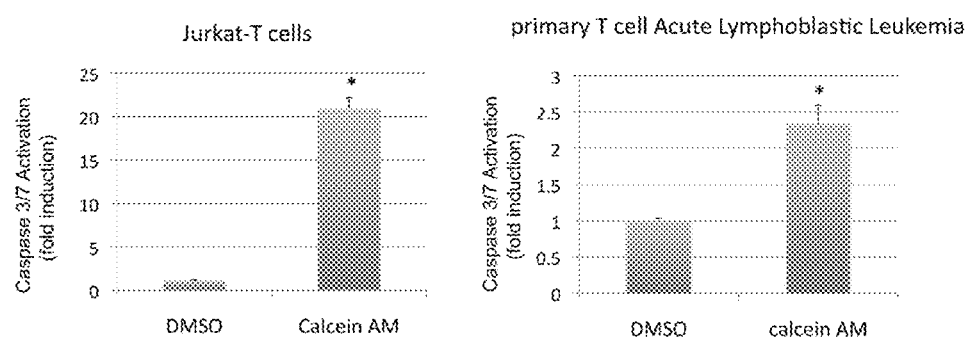

FIG. 13 Calcein AM is active in killing an established T cell leukemia cell line (Jurkat-T cell) and primary leukemia cells prepared from a patient with T cell acute lymphoblastic leukemia.

Jurkat-T cells and primary leukemia cells prepared from a patient with T cell acute lymphoblastic leukemia were treated with Calcein AM at 2.5 µM for 7 hours and then the induction of cell apoptosis was analyzed by caspase 3/7 activation assay. *, p<0.005, (compared with DMSO group)

Figure 14:
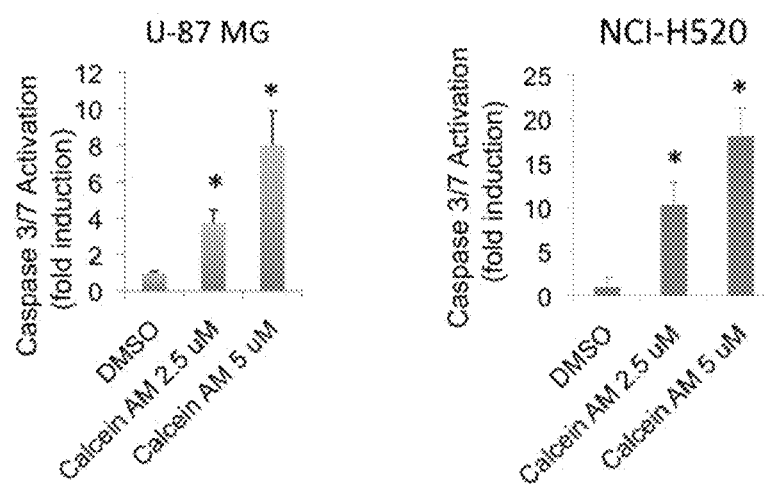

FIG. 14 Calcein AM induced apoptosis in glioblastoma multiforme (GBM) cells (U-87 MG) and lung cancer cells (NCI-H520).

U-87 cells (GBM cells) or NCI-H520 cells (lung cancer cells) were treated with Calcein AM at 2.5 or 5 µM for 16 hours and then the induction of cell apoptosis was analyzed by caspase 3/7 activation assay. *, p<0.005, (vs. DMSO group).

DETAILED DESCRIPTION OF THE PRESENTLY PREFERRED EMBODIMENTS

Methods
Cell Culture and Transfection

Human embryonic kidney cell lines HEK293 and HEK293T, human breast cancer cell lines MDA-MB468, MDA-MB231 and MCF7, human ovarian cancer cell line SKOV-3, human non-small cell lung cancer cell line NCI-H1299, mouse mammary carcinoma cell line 4T1 and rat hepatoma cell line McA-RH7777 were maintained in DMEM with 10% FBS. MCF10A, a normal human breast epithelial cell line, was maintained in DMEM/F12 with 5% horse serum, 2.5 mM glutamine, 0.5 µg/ml hydrocortisone, 10 µg/ml insulin, 100 ng/ml cholera toxin and 20 ng/ml EGF. Human breast cancer cell line BT549 and human myeloma cell line RPMI 8226 cells were maintained in RPMI with 10% FBS. All cell lines were obtained from ATCC and were tested negative for *mycoplasma* contamination. For maintenance, all cell lines were kept in 37° C. humidified incubator with 5% $CO_2$. For HEK293, HEK293T and NCI-H1299 cells standard calcium phosphate method was used for transfection. Polyethylenimine (PEI) was used to transfect MDA-MB468 cells and in some experiments of HEK293T cells. SKOV-3 cells were transfected by electroporation (Bio-Rad). BT549 cells were transfected using the Gene Pulser Xcell Electroporation System or PEI.

Virtual Screening and Docking

Schrödinger suite (version 2010, Schrödinger, LLC, New York, N.Y., 2010), which includes all of the programs described below, was used to carry out molecular modeling and docking studies. TopBP1-BRCT7/8 protein (PDB code: 3AL3) was prepared using the protein preparation wizard in Maestro 9.1 with default protein parameters: water molecules were removed, hydrogen atoms added and the BACH1 peptide ligand extracted for docking H-bonds were optimized and the protein was energetically minimized using OPLS2005 force field. A receptor grid, which is large enough to contain the whole active site, was generated using the program Glide without constraints.

2,000 compounds from Microsource Spectrum Collection were used for the virtual screening. Compound structures were prepared using the program LigPrep and then docked into the protein using Glide (docking parameters: standard-precision and dock flexibly). The top 100 compounds were analyzed manually, among which 61 compounds with M.W. greater than 250 were purchased from commercial vendors for further testing.

In Vitro Peptide Binding

The GST fusion proteins in *Escherichia coli* strain BL21 were induced by 0.1 mM IPTG (isopropyl-β-D-thiogalactopyranoside) and purified according to the standard protocol. The GST portion on GST-TopBP1-BRCT7/8 was excised by Pre-Scission protease (Pharmacia). Two purified (>98%) biotin conjugated peptides were synthesized from Sigma Genosys. The peptide sequence is derived from the surrounding sequence of TopBP1 S1159: pP, Btn-REERARLApSer$^{1159}$NLQWPS and nP, Btn-REERAR-LASNLQWPS. Purified TopBP1-BRCT7/8 (2 µg) was incubated with compounds in NETN-A buffer (50 mM NaCl, 1 mM EDTA, 20 mM Tris, 0.5% NP-40) at 4° C. for 3 h with constant rotation. Then 2 µg of purified pP or nP peptides were added and rotated for another 3 h at 4° C. The biotin-conjugated peptides were then pulled down with streptavidin-Sepharose (Amersham). The beads were washed six times with NETN-B buffer (100 mM NaCl, 1 mM EDTA, 0.2 mM phenylmethylsulfonyl fluoride) and then subjected to sodium dodecyl sulfate-polyacrylamide gel electrophoresis (SDS-PAGE) and analyzed by Western blotting with anti-TopBP1 antibody (1:1000, BL893, Bethyl Laboratories).

GST Pull-Down Assay

Purified TopBP1-BRCT7/8 (2 µg) was incubated with compounds in NETN-A buffer as above at 4° C. for 3 h with constant rotation. Then purified GST-p53-DBD or GST (2 µg) were added and rotated for another 3 h at 4° C. GST-p53-DBD was then pulled down with glutathione-Sepharose. The beads were washed six times with NETN-B buffer and then subjected to SDS-PAGE analysis.

Immunoprecipitation and Western Blot Analysis

MDA-MB468 cells were lysed with TNN buffer (Liu et al. 2003). An aliquot of cell lysates was lysed with SDS lysis buffer and the rest of cell lysates were incubated with appropriate antibodies or beads at 4° C. for 3-12 h. Anti-FLAG beads (Sigma) were washed three times with TNN buffer. Immunoprecipitates were fractionated by SDS-PAGE and electro-transferred to Immobilon-P membrane (Millipore). Equal amount of protein loading was validated with Ponceau-S staining. The specific signals were detected by incubating with appropriate antibody. All primary antibodies were used at 1:1000 dilution and horseradish peroxidase (HRP)-conjugated secondary antibodies were used at 1:5000 dilution for immunoblotting. E2F1 (C-20 and KH-95), p53 (FL393), p63 (4A4 and H-129), p73 (H-79), p21 (C-19), Bax (N-20), GST (B-14), c-Myc (A14), Miz1 (H-190), Chk1 (G4), Actin (C-2) and GAPDH (6C5) antibodies were purchased from Santa Cruz. TopBP1 (mouse monoclonal) and Aid antibodies were purchased from BD Transduction Laboratories. TopBP1 (BL893, Rabbit polyclonal) antibody was purchased from Bethyl. Mouse monoclonal anti-phospho-γH2AX was purchased from Millipore. Phospho-Chk1 (Ser345) antibody was purchased from Cell signaling. FLAG (F7425) antibody was purchased from Sigma. Mouse monoclonal anti-p73 (IMG-246) was purchased from IMGENEX.

Cross-Linking

Borate buffer (50 mM NaBorate, 100 mM potassium acetate, 2 mM $MgCl_2$, 1 mM EGTA, 1% Trition X-100, and protease inhibitors [pH 8.57]) was used to lyse MDA-MB468 cells on ice for 10 min. followed by 10 min high-speed centrifugation to remove insoluble material, and then incubated with 20 mM freshly prepared DMP (Dimethyl pimelimidate-2HCl, Thermo Scientific) for 30 min. An equal volume of 50 mM $NH_4Cl$ in PBS was added and incubated for 10 min to stop the reaction. The cell lysates were subjected to SDS-PAGE and Western blot analysis.

Luciferase Assay

E2F1 activity reporter assay using a p14$^{ARF}$ promoter-luciferase plasmid was performed as described (Liu et al. 2003). p53 activity reporter assay was performed by a p21$^{Cip}$ promoter-luciferase plasmid (Liu et al. 2009). p73 activity reporter assay was performed using a pGL3-Bax promoter-luciferase plasmid (Liu et al. 2011). pRL-TK (*Renilla* luciferase, Promega) was used in all experiments for controlling transfection efficiency. The firefly and *Renilla* luciferase activities were measured by Dual-Luciferase Reporter System (Promega), and the firefly luciferase activities were normalized against the *Renilla* activity. All assays were performed in triplicate.

Real Time RT-PCR

RNA was isolated using TRIzol method (Invitrogen). Quantitative reverse transcription-PCR (RT-PCR) was performed in triplicate using the forward and reverse primers ((Chowdhury et al. 2014) Supplementary FIG. 18) on an MX3005P thermal cycler using SYBR green dye method to observe the progress of the reactions with ROX dye, which was added as reference. GAPDH was run in parallel with target genes.

MTS Assay

Cells ($10^4$ cells/well) were plated into 48 well plates (BD Falcon) and treated with DMSO or Calcein AM separately. Then 50 μl of MTS reagent (CellTiter 96® AQueous One Solution Cell Proliferation Assay, Promega) was added to each well, covered from light and incubated for 1 h at 37.0 incubator to develop purple color. The samples were measured at 490 nm in a plate reader (BioTek Synergy HT) against a blank 48-well plate. Each assay was done in triplicate.

Caspase 3/7 Activation Assay

The apoptosis was measured by Caspase-Glo® 3/7 assay (Promega) following the manufacturer's protocol. The cells were plated in 6-well tissue culture dish ($10^4$ cells/well) (BD Falcon) in respective media. Next day the cells were treated with DMSO (as negative control) and Calcein AM for 5 h. The blank reactions were prepared per direction. Equal volume of Caspase-Glo® 3/7 reagents were applied to each well. A luminometer (Sirius) was used to quantitate luminescence.

Colony Formation Assay

MDA-MB468 cells were plated in 6-well plates at 200 cells/well. The cells were either treated DMSO vehicle or treated with indicated concentration of Calcein AM for 16 h and then released by 3 times 1×PBS washing. Cells were grown in fresh media without drugs for additional 8 days to form colonies, when each colony contained more than 50 cells. Plates were then stained with 5% crystal violet (0.5 g Crystal violet, 25 ml methanol and 75 ml $H_2O$). Cell number was counted.

Mammosphere Formation and Treatment

For in vitro mammosphere culture, ~5000 MDA-MB468 cells/well were seeded into a Ultra-low Adherent 6-well plate (Stem Cell Technologies) with 2 ml/well fresh complete MammoCult™ medium (Stem Cell Technologies) containing the MammoCult® Basal Medium, MammoCult® Proliferation Supplement, 4 μg/ml Heparin (Stem Cell Technologies) and fresh 0.48 μg/ml Hydrocortisone. Cells were incubated in a 5% $CO_2$ incubator at 37° C. for 7-11 days. Both the untreated (DMSO treated) and Calcein AM-treated mammospheres were observed at 10× magnification and measured on day 11 under a Zeiss digital Axio Observer inverted microscope. Each treatment was done in triplicate.

Gene Knockdown

To prepare TopBP1 knockdown stable cell line, MDA-MB468 cells were infected with lentivirus expressing TopBP1 shRNA (Liu et al. 2011) as well as scramble shRNA, separately. The infected cells were grown for 48 h followed by selection with puromycin (2 μg/ml). After selection, the knockdown was confirmed by Western blotting before further experiments. Two different pLKO-shTopBP1 (#1 and #2) constructs (Open Biosystems, RHS4533-NM_007027) were used to deplete TopBP1 in MDA-MB468 cells. Additional two pSuper-shTopBP1 constructs (Liu et al. 2004) were used to knock down TopBP1 in HEK293 cells. Two pSuper-shE2F1 constructs were used to deplete E2F1: shE2F1#1 (described previously (Liu et al. 2004)), and shE2F1#2 (target sequence 5'-GACTGT-GACTTTGGGGACC-3'). The target sequence for pSuperior-shE2F1 is the same as pSuper-shE2F1#1. To deplete p63, shp63alpha pLKO.1-puro (from Addgene, 19120) was used. TP73 MISSION shRNA (shp73 pLKO.1-puro) was purchased from Sigma (TRCN00002722587).

Xenograft Experiment

Female nu/nu mice (4-5 weeks old) were purchased from Charles River Laboratories (Cambridge, Mass.). The animals were cared for and maintained by the Animal Care and Use Committee of Baylor College of Medicine. Freshly grown MDA-MB468 breast cancer cells [($8\times10^6$) cells per site in 100 μl phosphate-buffered saline (PBS)] were injected subcutaneously into the right side of the flank of the 5-6 weeks old mice. When tumors were measurable, the mice were randomly divided into treatment and control groups. Calcein AM was dissolved in DMSO and was given intraperitoneally at 40 mg/kg for 3 doses every $3^{rd}$ day. The control group mice were injected with vehicle (DMSO) in the same way. The mice were monitored thrice per week. The weight of the mice and tumor size were measured on the indicated day with a caliper and calculated based on the formula π/6 (length×depth×width). The evaluator was blinded to the group allocation during monitoring. Animals were sacrificed in the indicated dates, and tumors were harvested, weighed, and further processed for histopathological analysis. All experiments were performed under a Baylor College of Medicine Institutional Animal Care and Use Committee (IACUC)-approved protocol and all experiments confirm to IACUC standards and ethical regulations.

Histology and Immunohistochemistry

Both control (DMSO) and Calcein AM treated tumor samples were placed in cassettes and fixed in 10% neutral buffered formalin for overnight. Next day the samples were sent to The Pathology and Histology Core of Baylor College of Medicine for further processing. The paraffin-embedded sections were stained with H&E, Ki-67, TUNEL and anti-cleaved caspase-3 using standard operating protocols.

Statistical Analyses

We performed two-tailed t test for comparisons of treatment groups. P values less than 0.05 were considered statistically significant. Pearson correlation coefficient was calculated to evaluate correlations between the mRNA expression of TopBP1 and Log $GI_{50}$ of Calcein AM in NCI-60 cell lines. The sample size of the xenograft study was chosen to detect 50% response rate of xenografts, and use 5% for type II error, then n=log 0.05/log 0.5=4.3. Thus, using 5 animals per group will have greater than 95% of statistical power.

Results

Calcein Blocks TopBP1 Oligomerization and Binding to E2F1 and p53.

Figure 1:
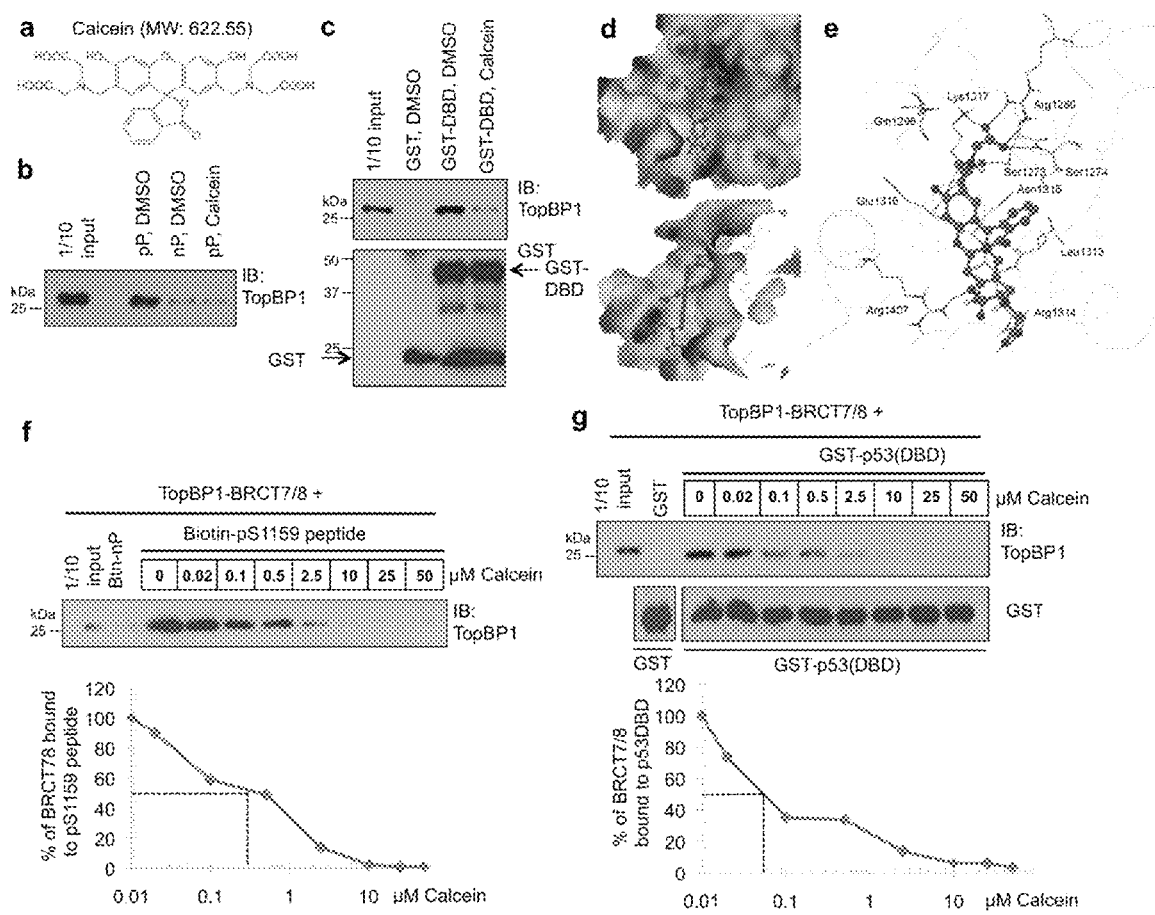
FIG. 1 Calcein binds TopBP1-BRCT7/8 and inhibits its binding to the pS1159 peptide and p53-DBD.
  (a) Structure of calcein, a fluorescent molecule with formula $C_{30}H_{26}N_2O_{13}$ and molecular weight 622.55.
  (b) Purified TopBP1-BRCT7/8 was incubated with DMSO or calcein and Btn-pS1159 peptide (pP) or nonphosphorylated peptide (nP), followed by streptavidin Sepharose pulldown as described in the Methods (Liu et al. 2006). The pulldown TopBP1-BRCT7/8 was analyzed by Western blotting (IB) with a TopBP1 antibody (BL893, Bethyl Laboratories) which recognizes the C-terminus of TopBP1. The result was replicated three times.
  (c) Purified TopBP1-BRCT7/8 was incubated GST-p53 (DBD) in the presence of DMSO or calcein, and GST pulldown assay was performed (Liu et al. 2009). This result was replicated four times.
  (d) The lowest-energy docking position of calcein (ball & stick model) in the structure of TopBP1-BRCT7/8 (shown as an electrostatic molecular surface), viewed from two different angles, shows favorable multiple polar and hydrophobic interactions between BRCT7/8 and calcein with a large aromatic system.
  (e) The interactions between the docked structure of calcein and the adjacent residues of TopBP1. H-bonds are shown as dotted lines.
  (f) Streptavidin Sepharose pulldown as in (b) was performed in the presence of various concentrations of calcein.
  (g) GST-p53(DBD) pulldown assay as in (c) was performed in the presence of various concentrations of calcein.
Figure 2:
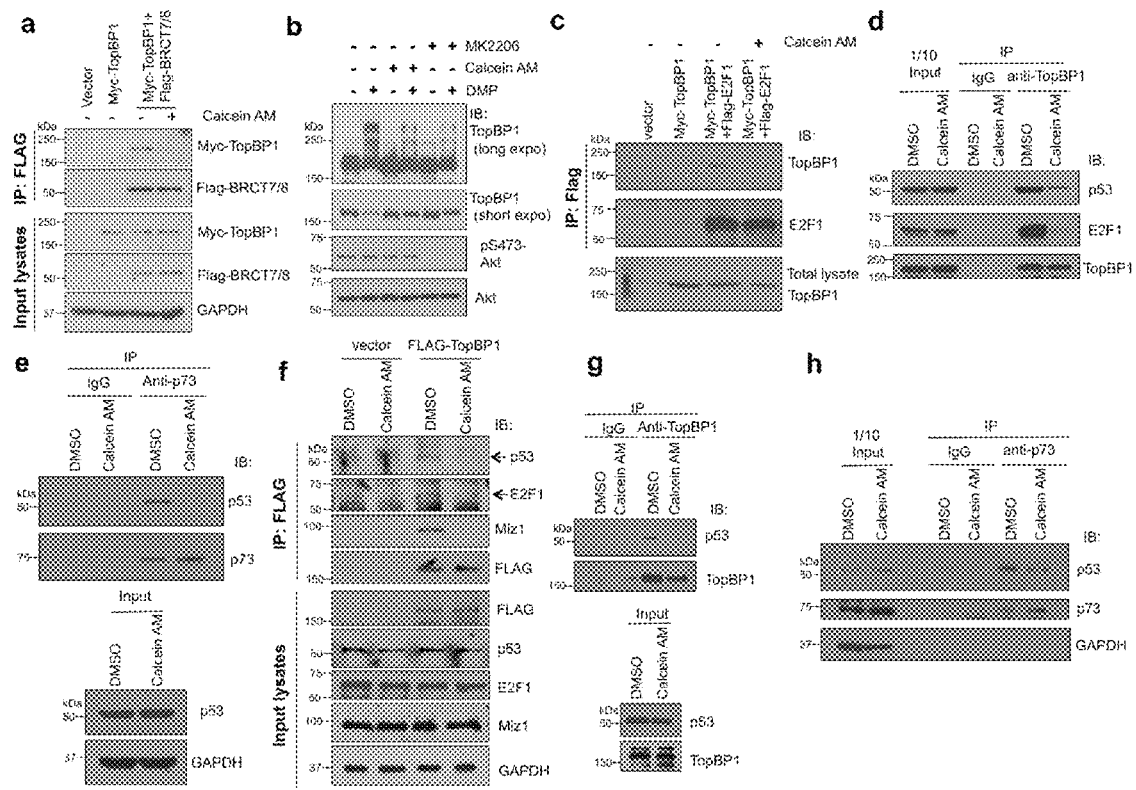
FIG. 2 Calcein inhibits TopBP1 oligomerization and binding to E2F1 and mutp53 and disrupts the interaction of mutp53 from p73.
  (a) MDA-MB468 cells were transfected with Myc-TopBP1 alone and in combination with FLAG-TopBP1-BRCT7/8. Cells were treated with Calcein AM (2.5 µM) or DMSO for 5 h. Cells were then lysed and immunoprecipitated with anti-FLAG beads followed by immunoblotting as described (Liu et al. 2013).
  (b) MDA-MB468 cells were treated with Calcein AM (2.5 µM) or DMSO for 5 h, and then lysed and incubated with 20 mM DMP for 30 min following the cross-linking protocol described in the Methods section. Cell lysates were analyzed by SDS-PAGE and immunoblotted with indicated antibodies. MK-2206 (1 µM for 24 h) served as a positive control (Liu et al. 2013). The result was replicated for two times.
  (c) HEK293 cells expressing Myc-TopBP1 and FLAG-E2F1 were treated with Calcein AM or DMSO for 5 h, followed by immunoprecipitation and immunoblotting as indicated.
  (d) MDA-MB468 cells were treated with Calcein AM (2.5 µM) or DMSO for 5 h. The cell lysates were then subjected to immunoprecipitation with anti-TopBP1 antibody or control mouse IgG and then immunoblotting to detect interacting mutp53 and E2F1. This result was replicated for three times.
  (e) MDA-MB468 cells were treated with Calcein AM (2.5 µM) or DMSO for 5 h. The cell lysates were then subjected to immunoprecipitation with anti-p73 antibody or control mouse IgG and then immunoblotting to detect mutp53.
  (f) BT549 cells were transfected with FLAG-TopBP1 or an empty vector. Two days later, cells were treated with Calcein AM (2.5 µM) or DMSO for 3 h and then harvested for anti-FLAG immunoprecipitation (Liu et al. 2013).
  (g) The interaction of endogenous TopBP1 and mutp53 in BT549 cells was examined by co-immunoprecipitation using anti-TopBP1 antibody or a control mouse IgG after cells were treated with Calcein AM (2.5 µM) or DMSO for 5 h.
  (h) BT549 cells were treated with Calcein AM (2.5 µM) or DMSO for 5 h, and then subjected to anti-p73 (or a control mouse IgG) immunoprecipitation.

Based on the mechanisms of action, we sought to design the TopBP1 inhibitors capable of blocking TopBP1 oligomerization and its interaction with mutp53. Since the BRCT7/8 domains of TopBP1 are responsible for both oligomerization and binding to p53 (Liu et al. 2009), and the BRCT domains form structured binding pockets, TopBP1-BRCT7/8 would be the ideal domains for screening compounds that block TopBP1 binding to pS1159 peptide and mutant p53. Using the TopBP1-BRCT7/8 structure (Leung et al. 2011), we performed a molecular docking screening to identify compounds that can bind to TopBP1-BRCT7/8. From a library of more than 2000 compounds including FDA-approved drugs (Microsource Spectrum Collection), we identified 61 compounds with top scores for fitting into the structural pocket of TopBP1-BRCT7/8 and with molecular weights of greater than 250 g. We then performed biochemical binding assays (pS1159 peptide binding assay (Liu et al. 2013) and GST-p53(DBD) pulldown assay (Liu et al. 2009)) to test the ability of these 61 compounds to block the interactions between TopBP1-BRCT7/8 and pS1159 peptide or p53(DBD). The compounds that showed activities in the initial screening were subjected to multiple independent binding assays for reproducibility. We identified an oxospiro-benzofuran derivative compound, calcein (FIG. 1a) that blocked the interactions of TopBP1-BRCT7/8 with pS1159 peptide (FIG. 1b) and p53(DBD) (FIG. 1c). The docking of calcein into TopBP1-BRCT7/8 pocket viewed from two different angles is shown in FIG. 1d&e. As seen from FIG. 1e, calcein is predicted to form H-bonds with K1317, R1280, S1273, S1274, R1314 and R1407, among which K1317 and S1273 had been demonstrated to be important for binding to pS1159 for oligomerization (Liu et al. 2013). We also tested these candidates in E2F1 activity reporter assay (Liu et al. 2003) and p53 activity reporter assay (Liu et al. 2009). Calcein is a hydrophilic fluorescent molecule that does not get into cells. Its non-fluorescent acetomethoxy derivative, Calcein AM (acetoxymethyl ester) can enter cells where it is hydrolyzed by esterases to calcein and retains inside the cells. We therefore used Calcein AM for cell culture experiments. Among these potential compounds, Calcein AM stood out in its ability to induce both E2F1 ((Chowdhury et al. 2014) Supplementary FIG. 1) and p53 activities ((Chowdhury et al. 2014) Supplementary FIG. 2). Both pS1159 peptide binding and GST-p53(DBD) pulldown assays showed that calcein blocked the TopBP1/pS1159 interaction (FIG. 1f) and TopBP1/p53(DBD) interaction (FIG. 1g) at submicromolar concentrations.

Ironically, Calcein AM is developed as a cell viability assay since only live cells can hydrolyze non-fluorescent Calcein AM into fluorescent calcein and retain calcein inside the cells. Calcein AM treatment was reported to have cytotoxic effect in some cancer cells (Liminga et al. 1995; Jonsson et al. 1996; Liminga et al. 2000); nevertheless, its detailed mechanisms of action remain unclear. We used Calcein AM to further investigate the in vivo effect of calcein in TopBP1 signaling. Since the interaction between TopBP1-BRCT7/8 and pS1159 peptide mediates TopBP1 oligomerization (Liu et al. 2013), Calcein AM was expected to block TopBP1 oligomerization. Indeed, using differentially tagged TopBP1, we found that Calcein AM (2.5 µM) was able to inhibit TopBP1 oligomerization in triple-negative, PTEN-null MDA-MB468 breast cancer cells (FIG. 2a). Calcein AM also blocked endogenous TopBP1 oligomerization in a DMP chemical crosslinking assay (Liu et al. 2013) (FIG. 2b). Here MK2206, an Akt allosteric inhibitor was used as a positive control for blocking Akt-dependent TopBP1 oligomerization (Liu et al. 2013). Importantly, Calcein AM not only inhibited the interaction between overexpressed E2F1 and TopBP1 in HEK293T cells (FIG. 2c), but also inhibited TopBP1/E2F1 and TopBP1/mutp53 interactions in MDA-MB468 cells (harboring mutp53 (R273H)) at physiological levels (FIG. 2d). TopBP1/mutp53 interaction has been shown to facilitate the binding of mutp53 to p63/p73 (Liu et al. 2011). Calcein AM treatment also led to release of p73 from mutp53 (FIG. 2e).

Previously, we showed that TopBP1 can interact with both "contact mutant" p53 (such as R273H) and conformational mutants (such as R175H and R249S) (Liu et al. 2011). Thus, we also tested Calcein AM in another triple-negative, PTEN-null breast cancer cell line BT549, which contains a conformational mutant R249S mutp53. Calcein AM treatment inhibited the interaction between TopBP1 and mutp53 and E2F1 in BT549 cells (FIG. 2f&g). Consistent with a role for TopBP1 oligomerization (Liu et al. 2006), Calcein AM also inhibited the interaction between TopBP1 and Miz1 (FIG. 2f), suggesting that the release of Miz1 from TopBP1 might mediate some of Calcein AM activities. Importantly, Calcein AM treatment also resulted in release of p73 from mutp53(R249S) in BT549 cells (FIG. 2h) like it did in MDA-MB468 cells.

Calcein AM Activates E2F1 and p53 and Blocks Mutp53 GOF.

Figure 3:
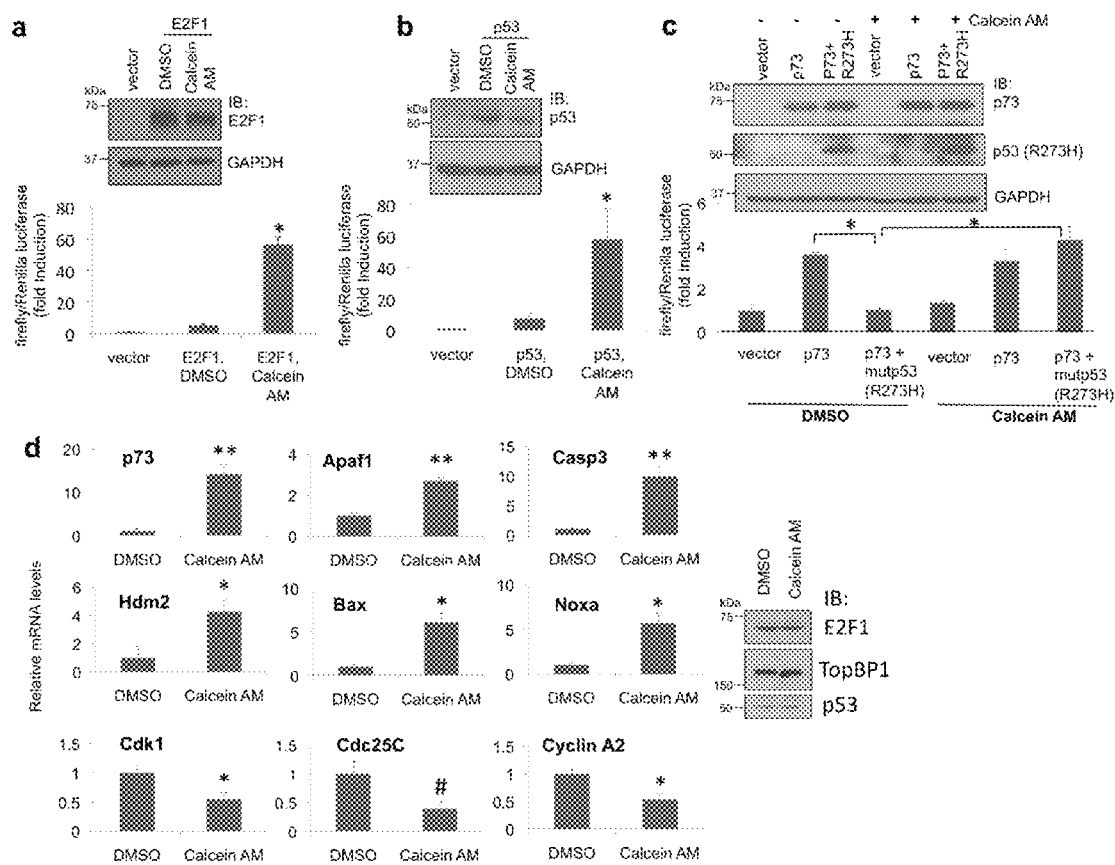
FIG. 3 Calcein AM induces E2F1 and p53 activities and blocks mutp53 gain of function.
  (a) E2F1 transcriptional activity was measured by a $p14^{Arf}$ promoter dual luciferase assay in HEK293 cells (Liu et al. 2003) after Calcein AM treatment. The normalized activities of E2F1 were shown as fold induction relative to that of the empty vector control. Results shown are the means±standard deviation (S.D.) from three independent experiments (biological replicates). *, P<0.001 (two-tailed t test).
  (b) p53 transcriptional activity was measured by a p21 promoter dual luciferase assay in H1299 cells (Liu et al. 2009) after Calcein AM treatment. The normalized activities of p53 (means±S.D. from three biological replicates) were shown as fold induction relative to that of the empty vector control. *, P<0.05 (two-tailed t test).
  (c) The effect of Calcein AM on mutp53(R273H) gain of function was measured in p53-null H1299 cells expressing p73α and mutp53 (R273H), along with a p73 activity reporter plasmid (a Bax promoter-luciferase plasmid) and pRL-TK as described (Liu et al. 2011). Luciferase activity of transfected p73 was determined as fold induction relative to that of the empty vector control (means±S.D. from three biological replicates). A portion of the cell lysates was subjected to immunoblotting with the indicated antibody (upper panel). *, P<0.001 (two-tailed t test).
  (d) MDA-MB468 cells were treated with Calcein AM as in FIG. 2d. RNA was then isolated for real-time RT-PCR analysis using primers specific to E2F1, p53 and NF-Y target genes or GAPDH. Results were normalized to GAPDH levels and the means±S.D. (n=3) are expressed relative to the expression of genes in control cells. Aliquots of the cell lysates were analyzed by immunoblotting (right panel). The experiment was performed in biological triplicates. **, P<0.001; *, P<0.01; #, P<0.05 (two-tailed t test).

Next, we examined the effect of Calcein AM on E2F1 and p53 transcriptional activities using E2F1 (Liu et al. 2003) and p53 activity reporter assay (Liu et al. 2009), respectively. In line with its effect on blocking TopBP1 function in repressing E2F1 and p53 activities, Calcein AM treatment enhanced E2F1 and p53 transcriptional activities (FIG. 3a-b). To demonstrate the induction of p14$^{Arf}$ promoter-luciferase activity by Calcein AM was indeed due to E2F1, we performed an independent assay using a pair of the p68 subunit of DNA polymerase a promoter constructs: pKL12 (containing two wild-type E2F sites) and pKL12-E2FAB (both E2F sites being mutated and no longer responding to E2F) (Nishikawa et al. 2000; Liu et al. 2003). Indeed, Calcein AM could only induce the activity on pKL12, but not on pKL12-E2FAB ((Chowdhury et al. 2014) Supplementary FIG. 3). To show the induction of p21 promoter activity by Calcein AM was dependent on p53, we used a pair of isogenic cell lines (Bunz et al. 1999) p53$^{+/+}$ and p53$^{-/-}$ HCT116 and showed that the induction of p21 and another p53 target Bax was observed on in p53$^{+/+}$, but not in p53$^{-/-}$ HCT116 cells ((Chowdhury et al. 2014) Supplementary FIG. 4). Previously using a p73 activity reporter (Bax-promoter-driven luciferase) assay, we found that in p53-null H1299 cells, overexpression of mutp53(R273H) blocked the p73 transcriptional activity in a TopBP1-dependent manner (Liu et al. 2011). Consistently, mutp53(R273H) inhibited p73 transcriptional activity, and indeed this activity was blocked by Calcein AM (FIG. 3c), indicating an inhibitory effect of Calcein AM on mutp53 GOF. To further investigate whether Calcein AM affected endogenous activities of E2F1 and mutant p53, we examined the target genes of E2F1, p63/p73 and NF-Y in MDA-MB468 cells. Calcein AM up-regulated E2F1 pro-apoptotic target genes, such as p'73, Apaf1 and caspase 3 in MDA-MB468 cells (FIG. 3d). Calcein AM also inhibited mutp53 GOF activities by up-regulation of p63/p73 target genes such as Bax, Noxa, Hdm2 and down-regulation of NF-Y target genes, such as Cdk1, Cdc25C and Cyclin A2 (Liu et al. 2011) (FIG. 3d). These data demonstrate that calcein binds TopBP1 to block mutp53 GOF and restore pro-apoptotic activities of E2F1 and p63/p73.

Calcein AM Kills TopBP1-Overexpressing Cancer Cells.

We then performed MTS assay to determine the cytotoxic activity of Calcein AM in three breast cancer cell lines MDA-MB468, MDA-MB231, MCF7 and a non-transformed MCF10A cell line. Calcein AM preferentially inhibited the proliferation of these three cancer cell lines (FIG. 4a). The caspase 3/7 activity assay showed that Calcein AM induced apoptosis in MCF7, MDA-MB231 and MDA-MB468 cells, but to a much lesser degree in MCF10A cells (FIG. 4b). When co-treated with doxorubicin (adriamycin), Calcein AM greatly enhanced the doxorubicin sensitivity in MDA-MB468, but not in MCF10A cells (FIG. 4c & (Chowdhury et al. 2014) Supplementary FIG. 5). Mutp53 GOF has been shown to expand the breast cancer stem cells (Lu et al. 2013), which form mammospheres in suspension culture (Dontu et al. 2003). The mammosphere formation of MDA-MB468 cells was also blocked by Calcein AM (FIG. 4d). It is possible that this is at least in part due to the cytotoxic activity of Calcein AM, but at the concentration used in this experiment, many cells still survived and could be scored ((Chowdhury et al. 2014) Supplementary FIG. 6), but they failed to form mammosphere. To further investigate the cytostatic (inhibiting proliferation) and cytotoxic (inducing apoptosis) activities of Calcein AM in a quantitative way, we performed colony formation assay (FIG. 4e & (Chowdhury et al. 2014) Supplementary FIG. 7) and caspase 3/7 activity assay (FIG. 4f) after treating MDA-MB468 cells with increasing doses of Calcein AM. While apoptosis was induced at 2.5 and 5 µM, but not at 0.1 and 0.5 µM, inhibition of colony formation was apparent at 0.1 µM and beyond. Thus, Calcein AM exerts its effect through its activity in suppressing proliferation and, when given at higher doses, inducing apoptosis.

We next extended the studies to other cancer cell lines. We found that Calcein AM also inhibited the proliferation of p53-null SKOV-3 ovarian cancer cells either alone (FIG. 5a) or in combination with cisplatin (FIG. 5b). Although overexpression of mutp53(R273H) inhibited cisplatin-induced apoptosis in SKOV-3 cells (due to mutp53 GOF (Liu et al. 2011)), this effect could be partially rescued by Calcein AM (FIG. 5c). Calcein AM also sensitized cells to doxorubicin in a myeloma cell line RPMI 8226 harboring mutp53(E285K) (FIG. 5d). Thus, Calcein AM appears to have activity against a broad spectrum of cancer cells. In fact, Calcein AM (NSC 689290) is among the active compounds in NCI Developmental Therapeutics Program (DTP) screening program, which utilized a panel of NCI-60 cancer cell lines to test compounds at five concentrations. The average Calcein AM $GI_{50}$ over all 60 cell lines is 0.662 µM (ranging from 10 nM to 10.96 µM, see FIG. 6a) (NCI-DTP data). The $GI_{50}$ of Calcein AM in several triple-negative breast cancer (TNBC) cell lines such as BT549 and Hs-578T, etc. are less than 0.4 µM, and in several lung cancer cell lines such as A549, NCI-H23, NCI-H460 and NCI-H522 are less than 1 µM (FIG. 6a). We analyzed Calcein AM sensitivity ($GI_{50}$) and TopBP1 RNA levels in NCI-60 cell lines from NCI-DTP server and found a correlation between high TopBP1 levels and the sensitivity Calcein AM (r=−0.4439, two tailed p=0.0005, FIG. 6b). Upon examining the Akt status (in RPPA database) of those cells with discordance (i.e. sensitivity does not correlate with TopBP1 expression), we found most of them show low Akt activity (low T308 phosphorylation), e.g. MDA-MB435 cells (DeGraffenried et al. 2004) (FIG. 6a). This suggested that the sensitivity to Calcein AM might be affected by both TopBP1 levels and Akt activity. To test this in an unbiased manner, we ranked the NCI-60 cell lines according to either pT308Akt or total Akt levels, and calculated the Pearson correlation coefficients. While total Akt status does not affect the correlation between TopBP1 and Calcein AM sensitivity, higher pT308Akt levels indeed show better correlation (FIG. 6c-d). Thus, Calcein AM has activity against a wide spectrum of cancer cells, and its sensitivity is correlated with TopBP1 levels, particularly in Akt-activated cancer cells.

E2F1 and p63/p73 Mediate Calcein AM Anti-Cancer Activity.

Since Calcein AM activates E2F1 pro-apoptotic target genes, blocks mutp53 GOF (FIG. 3) and releases p73 from mutp53 binding (FIG. 2), we examined whether the cytotoxic activity of Calcein AM was mediated by E2F1 and p63/p73 which were unleashed after Calcein AM interrupted TopBP1/E2F1 and TopBP1/mutp53 interactions. We chose BT549 for these studies due to their Calcein AM sensitivity and high transfection efficiency. Consistent with the low $GI_{50}$ of Calcein AM (0.27 µM, from NCI-DTP database, FIG. 6a) for BT549 cells, Calcein AM induced apoptosis in BT549 cells at 1 µM and above (FIG. 7a). Depletion of E2F1 by two shRNA constructs attenuated Calcein AM response as measured by caspase activation (FIG. 7b) and viability assay (FIG. 7c). Calcein AM-induced apoptosis was also decreased by depletion of p63 (FIG. 7d) and p73 (FIG. 7e). Correspondingly, there were more living cells in p63- and p73-depleted cells compared with scrambled shRNA after Calcein AM (FIG. 7f). Together with E2F1 and p63/p73 target gene analysis shown in FIG. 3d, these data indicate that Calcein AM activates E2F1 and p63/p73 activities to induce apoptosis.

A Novel TopBP1-Dependent Mechanism for Calcein AM Activity.

With the correlation between TopBP1 levels and Calcein AM sensitivity in NCI-60 cancer cell lines (FIG. 6), we investigated how TopBP1 levels affected Calcein AM response. Overexpression of TopBP1 in MDA-MB231 cells that express TopBP1 at lower levels rendered cells more resistant to doxorubicin. This result demonstrates the activity of TopBP1 in repressing doxorubicin-induced apoptosis. Importantly, this anti-apoptotic activity of TopBP1 was blocked by Calcein AM (FIG. 8a & (Chowdhury et al. 2014) Supplementary FIG. 8a). On the other hand, consistent with previous data on the up-regulation of E2F1- and p63/p73-dependent pro-apoptotic target gene expression by TopBP1 knockdown (Liu et al. 2006; Liu et al. 2011), TopBP1 depletion sensitized MDA-MB468 to doxorubicin treatment (FIG. 8b & (Chowdhury et al. 2014) Supplementary FIG. 8b). While Calcein AM sensitized the shScr control MDA-MB468 cells to doxorubicin, it failed to cast the same effect on TopBP1-depleted MDA-MB468 cells (FIG. 8b & (Chowdhury et al. 2014) Supplementary FIG. 8b). Acute depletion of TopBP1 in HEK293 cells induced E2F1-dependent apoptosis (Liu et al. 2004). Calcein AM also induced apoptosis in HEK293 cells (FIG. 8c). In the TopBP1-depleted HEK293 cells where E2F1 activity has been unleashed, Calcein AM could not induce more apoptosis (FIG. 8c). The data in FIG. 8a-c indicate that Calcein AM blocks TopBP1 anti-apoptotic activity and that Calcein AM and TopBP1 shRNAs were targeting the same molecules or pathways. Together with the analysis of NCI-60 cells lines in FIG. 6, these data support TopBP1 as an in vivo target for Calcein AM. To rule out the possibility that Calcein AM might cause DNA damage through other undefined mechanisms, we treated MDA-MB468 with this compound up to 10 µM and still did not see evidence of DNA damage as shown by lack of either pS15-p53 or γ-H2AX signal ((Chowdhury et al. 2014) Supplementary FIG. 9). We also examined whether Calcein AM might interfere with TopBP1 checkpoint activation. In fact, Calcein AM did not block HU-induced Chk1 activation ((Chowdhury et al. 2014) Supplementary FIG. 10), and might slightly promote Chk1 activation in a TopBP1-dependent manner. This is consistent with the effect of Calcein AM in blocking TopBP1 oligomerization and shifting TopBP1 toward monomeric form for checkpoint activation. Taken together, Calcein AM selectively kills cancer cells through a TopBP1-dependent mechanism of action.

Calcein AM Inhibits the Growth of Breast Cancer Xenografts.

To investigate the in vivo activity of Calcein AM, we next established MDA-MB468 xenografts in nude mice and injected i.p. with Calcein AM (40 mg/kg) or vehicle (DMSO) every three days for three doses (5 mice per group). Two independent experiments showed that Calcein AM significantly inhibited xenograft growth (FIGS. 9a-b and (Chowdhury et al. 2014) Supplementary FIG. 11) as well as the expression of proliferation marker Ki-67 (see Supplementary FIGS. 12-13 in paper (Chowdhury et al. 2014)) without affecting body weights of mice (FIG. 9c and (Chowdhury et al. 2014) Supplementary FIG. 11c). When the tumors started to regrow around day 60 in the experiment of (Chowdhury et al. 2014) Supplementary FIG. 11, a second round of treatment was given at day 61 since. The tumors responded to Calcein AM injection again. Immunohistochemistry of the xenografts harvested one week after the second injection showed inhibition of proliferation and induction of apoptosis, as indicated by Ki-67 staining, TUNEL assay and cleaved caspase 3 staining, respectively (FIG. 9d).

We also tested the in vivo activity of Calcein AM against the xenograft formation in another cell line BT549. Twenty nude mice were injected s.c. with BT549 cells. Four days later, mice were then injected i.p. either with DMSO (8 mice), Calcein AM 20 mg/kg (8 mice) or Calcein AM 40 mg/kg (4 mice) every three days for three doses. Six out of eight DMSO-treated mice developed xenografts later. On the contrary, none of the eight mice injected with Calcein AM 20 mg/kg and none of the four mice injected with Calcein AM 40 mg/kg developed tumors ((Chowdhury et al. 2014) Supplementary FIG. 14). Thus, Calcein AM has in vivo activity against tumor growth or development in MDA-MB468 and BT549 xenograft models.

The mice appeared to tolerate Calcein AM i.p. injections throughout the course of treatment. To investigate whether there was any acute toxicity in proliferating tissues, we injected Calcein AM 40 mg/kg and analyzed intestinal tissues 48 h after injection. As shown in (Chowdhury et al. 2014) Supplementary FIG. 15, Calcein AM injection did not decrease Ki-67 staining, nor did it induce apoptosis in the intestinal epithelium. The lack of toxicity in normal mouse tissues could be in principle due to a species-specific activity of Calcein AM against human cells, but not mouse cells. While this is unlikely since TopBP1-BRCT7/8 is highly conserved between human and mouse (74% identify, 83.3% similarity), and the predicted calcein contact residues K1317, R1280, S1273, S1274, R1314 and R1407 (FIG. 1e) are 100% conserved in mouse TopBP1. To rule out this possibility, we tested the activity of Calcein AM in mouse and rat tumor cells. As shown in (Chowdhury et al. 2014) supplementary FIG. 16, Calcein AM also induced apoptosis in mouse breast tumor cells 4T1 and rat hepatoma cells McA-RH7777. Thus, Calcein AM selectively kills cancer cells, but is not toxic to normal tissues.

We further utilized the MDA-MB468 cells expressing shTopBP1 to validate the in vivo target of Calcein AM. Indeed, depletion of TopBP1 mitigated the effect of Calcein AM on apoptosis (FIG. 9e; the results were reproduced in (Chowdhury et al. 2014) Supplementary FIG. 17 using two different shTopBP1). Correspondingly, the induction of E2F1, p63/p73 and NF-Y target gene expression by Calcein AM treatment was less significant in these TopBP1-depleted cells (FIG. 9f). We noted that in the TopBP1-depleted MDA-MB468 cells, E2F1 levels were reduced (FIG. 9g & (Chowdhury et al. 2014) Supplementary FIG. 17). It is possible that acute depletion of TopBP1 induces E2F1-dependent apoptosis (Liu et al. 2004), thus high E2F1 expressing cells would be counter-selected, resulting in selecting for the cells with lower E2F1 expression. To investigate the role for E2F1 in mediating the effect of TopBP1 depletion, we carried out doxycycline-inducible depletion of TopBP1 or both TopBP1 and E2F1 in U2OS cells (FIG. 10a) using U2OS T-REX system (Yang et al. 2008; Liu et al. 2009; Wang et al. 2010). The results show that upon depletion of TopBP1 after adding doxycycline (to induce TopBP1 shRNA), there was a decrease in cell number. This was a reversible and likely regulatory effect by TopBP1, since the defect was immediately rescued by restoring TopBP1 expression upon withdrawal of doxycycline. Thus, it is unlikely due to structural genomic damage from TopBP1 depletion. Importantly, the reduction in cell number by TopBP1 depletion was largely rescued upon concurrent depletion of E2F1 (FIG. 10a). This result indicates that the role of TopBP1 in cell proliferation/apoptosis is in part mediated through its regulation on E2F1. Therefore, Calcein AM sensitivity is affected by TopBP1 and E2F1 levels in cancer cells.

Taken together, Calcein AM targets TopBP1/E2F1 and TopBP1/mutp53 interactions and exerts its in vivo antitumor activity.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

REFERENCES

TCGA. 2008. Comprehensive genomic characterization defines human glioblastoma genes and core pathways. *Nature* 455: 1061-1068.

TCGA. 2012. Comprehensive molecular portraits of human breast tumours. *Nature* 490: 61-70.

Bourdon J C, Fernandes K, Murray-Zmijewski F, Liu G, Diot A, Xirodimas D P, Saville M K, Lane D P. 2005. p53 isoforms can regulate p53 transcriptional activity. *Genes Dev* 19: 2122-2137.

Bunz F, Hwang P M, Torrance C, Waldman T, Zhang Y, Dillehay L, Williams J, Lengauer C, Kinzler K W, Vogelstein B. 1999. Disruption of p53 in human cancer cells alters the responses to therapeutic agents. *J Clin Invest* 104: 263-269.

Chowdhury P, Lin G E, Liu K, Song Y, Lin F T, Lin W C. 2014. Targeting TopBP1 at a convergent point of multiple oncogenic pathways for cancer therapy. *Nat Commun* 5: 5476.

Collatz M B, Rudel R, Brinkmeier H. 1997. Intracellular calcium chelator BAPTA protects cells against toxic calcium overload but also alters physiological calcium responses. *Cell Calcium* 21: 453-459.

DeGraffenried L A, Fulcher L, Friedrichs W E, Grunwald V, Ray R B, Hidalgo M. 2004. Reduced PTEN expression in breast cancer cells confers susceptibility to inhibitors of the PI3 kinase/Akt pathway. *Ann Oncol* 15: 1510-1516.

Dontu G, Abdallah W M, Foley J M, Jackson K W, Clarke M F, Kawamura M J, Wicha M S. 2003. In vitro propagation and transcriptional profiling of human mammary stem/progenitor cells. *Genes Dev* 17: 1253-1270.

Forma E, Brzezianska E, Krzeslak A, Chwatko G, Jozwiak P, Szymczyk A, Smolarz B, Romanowicz-Makowska H, Rozanski W, Brys M. 2013a. Association between the c.*229C>T polymorphism of the topoisomerase IIbeta binding protein 1 (TopBP1) gene and breast cancer. *Mol Biol Rep* 40: 3493-3502.

Forma E, Wojcik-Krowiranda K, Jozwiak P, Szymczyk A, Bienkiewicz A, Brys M, Krzeslak A. 2013b. Topoisomerase IIbeta Binding Protein 1 c.*229C>T (rs115160714) Gene Polymorphism and Endometrial Cancer Risk. *Pathol Oncol Res*.

Freed-Pastor W A, Prives C. 2012. Mutant p53: one name, many proteins. *Genes Dev* 26: 1268-1286.

Garcia V, Furuya K, Carr A M. 2005. Identification and functional analysis of TopBP1 and its homologs. *DNA Repair (Amst)* 4: 1227-1239.

Herold S, Wanzel M, Beuger V, Frohme C, Beul D, Hillukkala T, Syvaoja J, Saluz H P, Haenel F, Eilers M. 2002. Negative Regulation of the Mammalian UV Response by Myc through Association with Miz-1. *Mol Cell* 10: 509-521.

Irwin M, Marin M C, Phillips A C, Seelan R S, Smith D I, Liu W, Flores E R, Tsai K Y, Jacks T, Vousden K H et al. 2000. Role for the p53 homologue p73 in E2F-1-induced apoptosis. *Nature* 407: 645-648.

Jonsson B, Liminga G, Csoka K, Fridborg H, Dhar S, Nygren P, Larsson R. 1996. Cytotoxic activity of calcein acetoxymethyl ester (Calcein/AM) on primary cultures of human haematological and solid tumours. *Eur J Cancer* 32A: 883-887.

Khoury M P, Bourdon J C. 2011. p53 Isoforms: An Intracellular Microprocessor? *Genes Cancer* 2: 453-465.

Leung C C, Gong Z, Chen J, Glover J N. 2011. Molecular basis of BACH1/FANCJ recognition by TopBP1 in DNA replication checkpoint control. *J Biol Chem* 286: 4292-4301.

Liminga G, Martinsson P, Jonsson B, Nygren P, Larsson R. 2000. Apoptosis induced by calcein acetoxymethyl ester in the human histiocytic lymphoma cell line U-937 GTB. *Biochem Pharmacol* 60: 1751-1759.

Liminga G, Nygren P, Dhar S, Nilsson K, Larsson R. 1995. Cytotoxic effect of calcein acetoxymethyl ester on human tumor cell lines: drug delivery by intracellular trapping. *Anticancer Drugs* 6: 578-585.

Lin W C, Lin F T, Nevins J R. 2001. Selective induction of E2F1 in response to DNA damage, mediated by ATM-dependent phosphorylation. *Genes Dev* 15: 1833-1844.

Liu K, Bellam N, Lin H Y, Wang B, Stockard C R, Grizzle W E, Lin W C. 2009. Regulation of p53 by TopBP1: a potential mechanism for p53 inactivation in cancer. *Mol Cell Biol* 29: 2673-2693.

Liu K, Graves J D, Scott J D, Li R, Lin W C. 2013. Akt switches TopBP1 function from checkpoint activation to transcriptional regulation through phosphoserine binding-mediated oligomerization. *Mol Cell Biol*.

Liu K, Lin F T, Ruppert J M, Lin W C. 2003. Regulation of E2F1 by BRCT-domain containing protein TopBP1. *Mol Cell Biol* 23: 3287-3304.

Liu K, Ling S, Lin W C. 2011. TopBP1 mediates mutant p53 gain of function through NF-Y and p63/p73. *Mol Cell Biol* 31: 4464-4481.

Liu K, Luo Y, Lin F T, Lin W C. 2004. TopBP1 recruits Brg1/Brm to repress E2F1-induced apoptosis, a novel pRb-independent and E2F1-specific control for cell survival. *Genes Dev* 18: 673-686.

Liu K, Paik J C, Wang B, Lin F T, Lin W C. 2006. Regulation of TopBP1 oligomerization by Akt/PKB for cell survival. *Embo J* 25: 4795-4807.

Lu X, Liu D P, Xu Y. 2013. The gain of function of p53 cancer mutant in promoting mammary tumorigenesis. *Oncogene* 32: 2900-2906.

Manfredi J J. 2010. The Mdm2-p53 relationship evolves: Mdm2 swings both ways as an oncogene and a tumor suppressor. *Genes Dev* 24: 1580-1589.

Marine J C, Francoz S, Maetens M, Wahl G, Toledo F, Lozano G. 2006. Keeping p53 in check: essential and synergistic functions of Mdm2 and Mdm4. *Cell Death Differ* 13: 927-934.

Metzeler K H, Hummel M, Bloomfield C D, Spiekermann K, Braess J, Sauerland M C, Heinecke A, Radmacher M, Marcucci G, Whitman S P et al. 2008. An 86-probe-set gene-expression signature predicts survival in cytogenetically normal acute myeloid leukemia. *Blood* 112: 4193-4201.

Muller H, Bracken A P, Vernell R, Moroni M C, Christians F, Grassilli E, Prosperini E, Vigo E, Oliner J D, Helin K. 2001. E2Fs regulate the expression of genes involved in differentiation, development, proliferation, and apoptosis. *Genes Dev* 15: 267-285.

Muller P A, Vousden K H. 2013. p53 mutations in cancer. *Nat Cell Biol* 15: 2-8.

Nahle Z, Polakoff J, Davuluri R V, McCurrach M E, Jacobson M D, Narita M, Zhang M Q, Lazebnik Y, Bar-Sagi D, Lowe S W. 2002. Direct coupling of the cell cycle and cell death machinery by E2F. *Nat Cell Biol* 4: 859-864.

Nishikawa N S, Izumi M, Uchida H, Yokoi M, Miyazawa H, Hanaoka F. 2000. Cloning and characterization of the 5'-upstream sequence governing the cell cycle-dependent transcription of mouse DNA polymerase alpha 68 kDa subunit gene. *Nucleic Acids Res* 28: 1525-1534.

Stiewe T, Putzer B M. 2000. Role of the p53-homologue p73 in E2F1-induced apoptosis. *Nat Genet* 26: 464-469.

Uggeri J, Gatti R, Belletti S, Scandroglio R, Corradini R, Rotoli B M, Orlandini G. 2004. Calcein-AM is a detector of intracellular oxidative activity. *Histochem Cell Biol* 122: 499-505.

Verhaak R G, Wouters B J, Erpelinck C A, Abbas S, Beverloo H B, Lugthart S, Lowenberg B, Delwel R, Valk P J. 2009. Prediction of molecular subtypes in acute myeloid leukemia based on gene expression profiling. *Haematologica* 94: 131-134.

Wang B, Liu K, Lin H Y, Bellam N, Ling S, Lin W C. 2010. 14-3-3Tau regulates ubiquitin-independent proteasomal degradation of p21, a novel mechanism of p21 downregulation in breast cancer. *Mol Cell Biol* 30: 1508-1527.

Yang S Z, Lin F T, Lin W C. 2008. MCPH1/BRIT1 cooperates with E2F1 in the activation of checkpoint, DNA repair and apoptosis. *EMBO Rep* 9: 907-915.

We claim:

1. A method of sensitizing cancer cells to a chemotherapeutic agent in a patient suffering from cancer by administering an effective amount of a small molecule inhibitor selected from the group consisting of Calcein and Calcein AM that binds the BRCT7/8 domain of TopBP1.

2. The method of claim 1 wherein the chemotherapeutic agent is doxorubicin or cisplatin.

3. The method of claim 1, wherein the cancer cells overexpress TopBP1.

* * * * *